US007655628B2

(12) United States Patent
Plater-Zyberk et al.

(10) Patent No.: US 7,655,628 B2
(45) Date of Patent: *Feb. 2, 2010

(54) METHOD FOR TREATING LIVER CIRRHOSIS OR INTERSTITIAL PULMONARY FIBROSIS

(75) Inventors: Christine Plater-Zyberk, Carouge (CH); Christine Power, Thoiry (FR); Jacques Colinge, Neydens (FR)

(73) Assignee: Merck Serono SA, Coinsins, Vaud (CH)

( * ) Notice: Subject to any disclaimer, the term of this patent is extended or adjusted under 35 U.S.C. 154(b) by 82 days.

This patent is subject to a terminal disclaimer.

(21) Appl. No.: 11/961,033

(22) Filed: Dec. 20, 2007

(65) Prior Publication Data

US 2008/0107627 A1    May 8, 2008

Related U.S. Application Data

(63) Continuation of application No. 10/432,256, filed as application No. PCT/EP01/13992 on Nov. 30, 2001, now Pat. No. 7,341,995.

(30) Foreign Application Priority Data

Dec. 6, 2000  (EP) .................................. 00126771
Aug. 17, 2001  (EP) .................................. 01118888

(51) Int. Cl.
*A61K 38/00* (2006.01)
(52) U.S. Cl. ........................ 514/12; 530/350; 530/351
(58) Field of Classification Search ........................ None
See application file for complete search history.

(56) References Cited

U.S. PATENT DOCUMENTS

| 5,266,575 | A | 11/1993 | Gerster et al. |
| 5,747,639 | A | 5/1998 | Seely |
| 5,858,715 | A | 1/1999 | Surya et al. |
| 6,800,735 | B2 | 10/2004 | Whitty et al. |
| 7,026,445 | B2 | 4/2006 | LaVallie et al. |
| 7,045,596 | B2 | 5/2006 | Umansky et al. |

FOREIGN PATENT DOCUMENTS

| EP | 0328255 A | 8/1989 |
| WO | WO 9801555 A | 1/1998 |
| WO | WO 9813493 A | 4/1998 |
| WO | WO 9835043 A | 8/1998 |

OTHER PUBLICATIONS

Abraham et al., "Expression and Function of Surface Antigens on Scleroderma Fibroblasts" *Arthritis and Rheumatism*, 34 (9): 1164-1172.
Abraham et al., "Expression and Function of Surface Antigens on Scleroderma Fibroblasts"; *Arthritis and Rheumatism*, 34 (9): 1164-1172, Sep. 1991.

Adler et al., "Allelic Variation at the *frizzled* Locus of *Drosopphilia*" *Molecular Biology Institute and Cancer Center*, 8:99-119 (1987); Charlottesville, University of Virginia.
Altschul et al., "Basic Local Alignment Search Tool"; *J. Mol. Biol.* (1990) 215:403-410; Academic Press Limited.
Altschul et al., Stephen F., "Gapped Blast and Psi-Blast: a new generation of protein database search programs" *Nucleic Acids Research* (1997) 25 (17): 3389-3402.
Bafico et al., "Interaction of Frizzled Related Protein (FRP) with Wnt Ligands and the Frizzled Receptor Suggests Alternative Mechanisms for FRP Inhibition of Wnt Signaling," *The Journal of Biological Chemistry*, 274(23): 16180-16187 (Jun. 4, 1999); The American Society for Biochemistry and Molecular Biology, Inc.
Bányai et al., "The NTR module: Domains of netrins, secreted frizzled related proteins, and type I procollagen C-proteinase enhancer protein are homologous with tissue inhibitors of metalloproteases," *Protein Science* (1990), 8:1636-1642; Cambridge University Press, USA.
Cavalli et al., "The Stress-Induced MAP Kinase p38 Regulates Endocytic Trafficking via the GDI:Rab5 Complex," *Molecular Cell*, 7: 421-432 (Feb. 2000); Cell Press.
Chang et al., "Cloning and characterization of a secreted frizzled-related protein that is expressed by the retinal pigment epithelium," *Human Molecular Genetics* (1999) 8(4): 575-583; Oxford University Press.
Devereux et al., "A comprehensive set of sequence analysis programs for the VAX," *Nucleic Acids Research*, 12(1) (1984); Laboratory of Genetics, University of Wisconsin, Madison, WI.
Dimmeler et al., "Oxidized Low-Density Lipoprotein Induces Apoptosis of Human Endothelial Cells by Activation of CPP32-Like Proteases: A Mechanistic Clue to the 'Reponse to Injury' Hypothesis" (Feb. 20, 1997), *Molecular Cardiology*, Department of Internal Medicinel IV, Univ. of Frankfurt; American Heart Association, Inc.
Finch et al., "Purification and molecular cloning of a secreted, Frizzled-related antagonist of Wnt action," *Proc. Natl. Acad. Sci. USA*, 94: 6770-6775 (Jun. 1997).
Golub et al., "Molecular Classification of Cancer: Class Discovery and Class Prediction by Gene Expression Monitoring," *Science*, 286: 531-537 (Oct. 15, 1999).
Grantham, "Amino Acid Formula to Help Explain Protein Evolution"; *Science* 16: 862-864 (Sep. 6, 1974).
Hattori et al., "Bleomycin-induced pulmonary fibrosis in fibrinogen-null mice"; *The Journal of Clinical Investigation*, 106 (11): 1341-1350 (Dec. 2000).
Krein et al., "Growth factor regulation and manipulation in wound repair: to scar or not to scar, that is the question," *Expert Opinion, Monthly Focus*: Pulmonary-Allergy, Dermatological, Gastrointestinal & Arthritis, pp. 1065-1079; Ashley Publications Ltd., 2001.

(Continued)

*Primary Examiner*—Robert Landsman
*Assistant Examiner*—Gyan Chandra
(74) *Attorney, Agent, or Firm*—Browdy and Neimark, PLLC

(57) ABSTRACT

The invention relates to the use of SARP-1 for the preparation of a medicament for the treatment and/or prevention of scleroderma, in particular of systemic sclerosis.

9 Claims, 11 Drawing Sheets

OTHER PUBLICATIONS

Leighton, "Drug Treatment of Scleroderma"; *Therapy in Practice, Drugs* (2001) 61 (3): 419-427; Adis International Limited.

Leimeister et al., "Developmental expression patterns of mouse sFRP genes encoding members of the secreted frizzled related protein family," *Mechanisms of Development* (1998) 75: 29-42; Elsevier Science Ireland Ltd.

Leroy et al., "Increased Collagen Synthesis by Scleroderma Skin Fibroblasts In Vitro," *The Journal of Clinical Investigation* 54: 880-889 (Oct. 1974).

Lin et al., "The cysteine-rich frizzled domain of Frzb-1 is required and sufficient for modulation of Wnt signaling," *Proc. Natl. Acad. Sci. USA* 94: 11196-11200 (Oct. 1997); The National Academy of Sciences.

Martini et al., "Marked and sustained improvement two years after autologous stem cell transplantation in a girl with systemic sclerosis"; *Arthritis & Rheumatism*, vol. 42, No. 4, Apr. 1999, pp. 807-811; American College of Rheumatology.

McCormick et al., "Anti-TGF-β Treatment Prevents Skin and Lung Fibrosis in Murine Sclerodermatous Graft-Versus-Host Disease: A Model for Human Scleroderma," *The American Association of Immunologists*, pp. 5693-5699 (1999).

Melkonyan et al., "SARPs: A family of secreted apoptosis-related proteins," *Proc. Natl. Acad. Sci, USA*, 94: 13636-13641 (Dec. 1997); Cell Biology.

Miller et al., "Mechanism and function of signal transduction by the Wnt/β-catenin and Wnt/Ca2+ pathways" *Oncogene* (1999), 18: 7860-7872; Stockton Press, 1999.

Mir et al., "High-efficiency gene transfer into skeletal muscle mediate by electric pulses," *Proc. Natl. Acad. Sci. USA*, 96: 4362-4267 (Apr. 1999).

Pearson, "Rapid and Sensitive Sequence Comparison with FASTP and FASTA" *Methods in Enzymology* 183: 63-98; Acedemic Press, Inc. 1990.

Pearson, "Improved tools for biological sequence comparison". *Proc. Natl. Acad. Sci. USA* 85:2444-2448.

Schumann et al., "Altered Expression of Secreted Apoptosis Related Proteins (SARPs) in Failing Human Myocardium Suggests Autocrine Modulation of Wnt/Frizzled Signaling by Cardiac Overload," *Circulation* 110(18): I-759 (Nov. 2, 1999).

Shevchenko et al., "Mass Spectormetric Sequencing of Proteins from Silver-Stained Polycrylamide Gels," *Anal. Chem.* (Mar. 1, 1996) 68: 850-858; American Chemical Society.Rattner, Amir, "A family of secreted proteins contains homology to the cysteine-rich ligand-binding domain of frizzled receptors"; Proc. Natl. Acad. Sci., USA, vol. 94, pp. 2859-.

Shi-Wen et al., "Scleroderma lung fibroblasts exhibit elevated and dysreglated type 1 collagen biosynthesis," *Arthritis & Rheumatism* 40 (7): 1237-1244 (Jul. 7, 1997); American College of Rheumatology.

Shi-Wen et al., "Fibroblast Matrix Gene Expression and Connective Tissue Remodeling: Role of Endothelin-1," *The Journal of Investigative Dermatology* (Nov. 22, 2000) 417-425.

Silman, "Mortality from scleroderma in England and Wales 1968-1985," *Annals of the Rheumatic Diseases* (1991) 50: 95-96.

Smalley et al., "Wnt signaling in mammalian development and cancer," *Cancer and Metastasis Reviews* 18: 215-230 (1999); Kluwer Academic Publishers, Netherlands.

Smith et al., "Identification of Common Molecular Subsequences," *J. Mol. Biol.* (1981) 147: 195-197.

Strehlow et al., "Biology of the scleroderma fibroblast," *Current Opinion in Rheumatology* (1998) 10: 572-578; Lippincott Williams & Wilkins.

Sule et al., "Update on Management of Scleroderma," *Bulletin on the Rheumatic Diseases*, Arthritis Foundation 49 (10): 1-4 (Feb. 20, 2000).

Von Heijene, "A new method for predicting signal sequence cleavage sites," *Nucleic Acids Research* (May 5, 1986) 14 (11): 4683-4690.

Wigley et al., "Novel therapy in the treatment of scleroderma" *Expert Opinion on Investigational Drugs* (2001) 10(1): 31-48; Ashley Publications Ltd.

Wilm et al., "Femtomole sequencing of proteins from polyacrylamide gels by nano-electrospray mass spectrometry," *Letters to Nature* (Feb. 1, 1996) 379:466-469.

Yamamoto et al., "Anti-sclerotic Effect of Transforming Growth Factorβ Antibody in a Mouse Model of Bleomycin-Induced Scleroderma," *Clinical Immunology* 92 (1): 6-13 (1999); Acedemic Press.

Kawakami "Increased Expression of TGF-β Receptors by Scleroderma Fibroblasts: Evidence for Contribution of Autocrine TGF-β Signaling to Scleroderma Phenotype" *The Journal of Investigative Dermatology* 110 (1): 47-51 (Jan. 1998).

Hu et al., Tissue restricted expression of two human Frzbs in preadipocytes and pancreas, *Biochemical and Biophysical Research Communications*, 247:287-293 (1998).

Ladher et al., Cloning and expression of the Wnt antagonists Sfrp-2 and Frzb during chick development, *Developmental Biology*, 218:183-198 (2000).

Dann CE, Hsieh JC, Rattner A, Sharma D, Nathans J, Leahy 1IJ, Insights into Wnt binding and signalling from the structures of two Frizzled cysteine-rich domains, *Nature.* Jul. 5, 2001;412(6842):86-90.

Marshall SA, Lazar GA, Chirino AJ, Desjarlais JR, Rational design and engineering of therapeulic proteins, *Drug Discov Today.* Mar. 1, 2003;8(5):212-21.

Chuang VT, Kragh-Hansen U, Otagir i Ad, Pharmaceutical strategies utilizing recombinant human serum albumin, *Pharm Res.* May 2002; 19(3):569-77.

Iffland A, Tqfelmeyer P, Saudan C, Johnsson K, Directed molecular evolution of cytochrome c peroxidase, *Biochemistry.* Sep. 5, 2000;39(35): 10790-8.

Jermutus L, Osborn JK, How do you jhd new drugs using polypeptide display?, *Trends Biotechnol.* Jul. 2000; 18(7):280-1.

Forrer P, Jung S, Pluckthun A, Beyond binding: using phage display to select for structure, folding and enzymatic activity in protein, *Curr Opin Struct Biol.* Aug. 1999;9(4):514-20.

Rattner A, Hsieh J, Smallwood PM, Gilbert DJ, Copeland NG, Jenkins NA, and Nathans J, A family of secreted proteins contains homology to the cysteine-rich ligand-binding domain for frizzled receptors, *Proc Natl Acad Sci USA,* Apr. 1997 94;2859-2863.

Wells, *Biochemistry*, 29:8509-8517 (1990).

```
     GCCAAGCTTCCCACGATGCTGCAGGGCCCTGGCTCGCTGCTGCTGCTCTTCCTCGCCTCG
   1 ------------+---------+---------+---------+---------+---------+ 60
     CGGTTCGAAGGGTGCTACGACGTCCCGGGACCGAGCGACGACGACGAGAAGGAGCGGAGC a              M  L  Q  G  P  G  S  L  L  L  L  F  L  A  S    -

CACTGCTGCCTGGGCTCGGCGCGCGGGCTCTTCCTCTTTGGCCAGCCCGACTTCTCCTAC
  61 ------------+---------+---------+---------+---------+---------+ 120
     GTGACGACGGACCCGAGCCGCGCGCCCGAGAAGGAGAAACCGGTCGGGCTGAAGAGGATG a     H  C  C  L  G  S  A  R  G  L  F  L  F  G  Q  P  D  F  S  Y  -
                    ↑              ↑

AAGCGCAGCAATTGCAAGCCCATCCCGGCCAACCTGCAGCTGTGCCACGGCATCGAATAC
 121 ------------+---------+---------+---------+---------+---------+ 180
     TTCGCGTCGTTAACGTTCGGGTAGGGCCGGTTGGACGTCGACACGGTGCCGTAGCTTATG a     K  R  S  N  C  K  P  I  P  A  N  L  Q  L  C  H  G  I  E  Y  -

CAGAACATGCGGCTGCCCAACCTGCTGGGCCACGAGACCATGAAGGAGGTGCTGGAGCAG
 181 ------------+---------+---------+---------+---------+---------+ 240
     GTCTTGTACGCCGACGGGTTGGACGACCCGGTGCTCTGGTACTTCCTCCACGACCTCGTC a     Q  N  M  R  L  P  N  L  L  G  H  E  T  M  K  E  V  L  E  Q  -

GCCGGCGCTTGGATCCCGCTGGTCATGAAGCAGTGCCACCCGGACACCAAGAAGTTCCTG
 241 ------------+---------+---------+---------+---------+---------+ 300
     CGGCCGCGAACCTAGGGCGACCAGTACTTCGTCACGGTGGGCCTGTGGTTCTTCAAGGAC a     A  G  A  W  I  P  L  V  M  K  Q  C  H  P  D  T  K  K  F  L  -

TGCTCGCTCTTCGCCCCCGTCTGCCTCGATGACCTAGACGAGACCATCCAGCCATGCCAC
 301 ------------+---------+---------+---------+---------+---------+ 360
     ACGAGCGAGAAGCGGGGGCAGACGGAGCTACTGGATCTGCTCTGGTAGGTCGGTACGGTG a     C  S  L  F  A  P  V  C  L  D  D  L  D  E  T  I  Q  P  C  H  -

TCGCTCTGCGTGCAGGTGAAGGACCGCTGCGCCCCGGTCATGTCCGCCTTCGGCTTCCCC
 361 ------------+---------+---------+---------+---------+---------+ 420
     AGCGAGACGCACGTCCACTTCCTGGCGACGCGGGGCCAGTACAGGCGGAAGCCGAAGGGG a     S  L  C  V  Q  V  K  D  R  C  A  P  V  M  S  A  F  G  F  P  -

TGGCCCGACATGCTTGAGTGCGACCGTTTCCCCCAGGACAACGACCTTTGCATCCCCCTC
 421 ------------+---------+---------+---------+---------+---------+ 480
     ACCGGGCTGTACGAACTCACGCTGGCAAAGGGGGTCCTGTTGCTGGAAACGTAGGGGGAG a     W  P  D  M  L  E  C  D  R  F  P  Q  D  N  D  L  C  I  P  L  -

GCTAGCAGCGACCACCTCCTGCCAGCCACCGAGGAAGCTCCAAAGGTATGTGAAGCCTGC
 481 ------------+---------+---------+---------+---------+---------+ 540
     CGATCGTCGCTGGTGGAGGACGGTCGGTGGCTCCTTCGAGGTTTCCATACACTTCGGACG a     A  S  S  D  H  L  L  P  A  T  E  E  A  P  K  V  C  E  A  C  -
```

Fig. 5A

```
            AAAAATAAAAATGATGATGACAACGACATAATGGAAACGCTTTGTAAAAATGATTTTGCA
        541 ---------+---------+---------+---------+---------+---------+ 600
            TTTTTATTTTTACTACTACTGTTGCTGTATTACCTTTGCGAAACATTTTTACTAAAACGT
a           K  N  K  N  D  D  D  N  D  I  M  E  T  L  C  K  N  D  F  A   -

CTGAAAATAAAAGTGAAGGAGATAACCTACATCAACCGAGATACCAAAATCATCCTGGAG
        601 ---------+---------+---------+---------+---------+---------+ 660
            GACTTTTATTTTCACTTCCTCTATTGGATGTAGTTGGCTCTATGGTTTTAGTAGGACCTC
a           L  K  I  K  V  K  E  I  T  Y  I  N  R  D  T  K  I  I  L  E   -

ACCAAGAGCAAGACCATTTACAAGCTGAACGGTGTGTCCGAAAGGGACCTGAAGAAATCG
        661 ---------+---------+---------+---------+---------+---------+ 720
            TGGTTCTCGTTCTGGTAAATGTTCGACTTGCCACACAGGCTTTCCCTGGACTTCTTTAGC
a           T  K  S  K  T  I  Y  K  L  N  G  V  S  E  R  D  L  K  K  S   -

GTGCTGTGGCTCAAAGACAGCTTGCAGTGCACCTGTGAGGAGATGAACGACATCAACGCG
        721 ---------+---------+---------+---------+---------+---------+ 780
            CACGACACCGAGTTTCTGTCGAACGTCACGTGGACACTCCTCTACTTGCTGTAGTTGCGC
a           V  L  W  L  K  D  S  L  Q  C  T  C  E  E  M  N  D  I  N  A   -

CCCTATCTGGTCATGGGACAGAAACAGGGTGGGGAGCTGGTGATCACCTCGGTGAAGCGG
        781 ---------+---------+---------+---------+---------+---------+ 840
            GGGATAGACCAGTACCCTGTCTTTGTCCCACCCCTCGACCACTAGTGGAGCCACTTCGCC
a           P  Y  L  V  M  G  Q  K  Q  G  G  E  L  V  I  T  S  V  K  R   -

TGGCAGAAGGGGCAGAGAGAGTTCAAGCGCATCTCCCGCAGCATCCGCAAGCTGCAGTGC
        841 ---------+---------+---------+---------+---------+---------+ 900
            ACCGTCTTCCCCGTCTCTCTCAAGTTCGCGTAGAGGGCGTCGTAGGCGTTCGACGTCACG
a           W  Q  K  G  Q  R  E  F  K  R  I  S  R  S  I  R  K  L  Q  C   -

TAGCTCGAGCGC
        901 ---------+-- 912
            ATCGAGCTCGCG
```

Fig. 5 B

| | |
|---|---|
| HUMAN | MLQGPGSLLLLFLASHCCLGSARGLFLFGQPDFSYKRSNCKPIPANLQLCHGIEYQNMRL |
| MOUSE | MPRGPASLLLLVLASHCCLGSARGLFLFGQPDFSYKRSNCKPIPANLQLCHGIEYQNMRL |
| | *.** ***** ********************************************** |
| HUMAN | PNLLGHETMKEVLEQAGAWIPLVMKQCHPDTKKFLCSLFAPVCLDDLDETIQPCHSLCVQ |
| MOUSE | PNLLGHETMKEVLEQAGAWIPLVMKQCHPDTKKFLCSLFAPVCLDDLDETIQPCHSLCVQ |
| | ************************************************************ |
| HUMAN | VKDRCAPVMSAFGFPWPDMLECDRFPQDNDLCIPLASSDHLLPATEEAPKVCEACKNKND |
| MOUSE | VKDRCAPVMSAFGFPWPDMLECDRFPQDNDLCIPLASSDHLLPATEEAPKVCEACKTKNE |
| | ******************************************************* ** |
| HUMAN | DDNDIMETLCKNDFALKIKVKEITYINRDTKIILETKSKTIYKLNGVSERDLKKSVLWLK |
| MOUSE | DDNDIMETLCKNDFALKIKVKEITYINRDTKIILETKSKTIYKLNGVSERDLKKSVLWLK |
| | ************************************************************ |
| HUMAN | DSLQCTCEEMNDINAPYLVMGQKQGGELVITSVKRWQKGQREFKRISRSIRKLQC |
| MOUSE | DSLQCTCEEMNDINAPYLVMGQKQGGELVITSVKRWQKGQREFKRISRSIRKLQC |
| | ****************************************************** |

Fig. 6

METHOD FOR TREATING LIVER CIRRHOSIS OR INTERSTITIAL PULMONARY FIBROSIS

CROSS-REFERENCE TO RELATED APPLICATIONS

The present application is a continuation of application Ser. No. 10/432,256, Oct. 7, 2003 now issued as U.S. Pat. No. 7,341,995, which is a 371 national stage of PCT/EP01/13992, filed Nov. 30, 2001, which claims priority from EP 00126771.5, filed Dec. 6, 2000, and EP 01118888.5, filed Aug. 17, 2001. The entire contents of prior applications are herein incorporated by reference.

FIELD OF THE INVENTION

The present invention is in the field of scleroderma. More specifically, the invention relates to the use of SARP-1 for the treatment and/or prevention of scleroderma, in particular of systemic sclerosis.

BACKGROUND OF THE INVENTION

Scleroderma is a disease of the connective tissue characterized by fibrosis of the skin and internal organs, leading to organ failure and death (Black et al., 1998; Clements and Furst, 1996). Scleroderma has a spectrum of manifestations and a variety of therapeutic implications. It comprises localized scleroderma, systemic sclerosis, scleroderma-like disorders, and Sine scleroderma (Smith, 2000). Whilst localized scleroderma is a rare dermatologic disease associated with fibrosis and manifestations limited to skin, systemic sclerosis is a multisystem disease with variable risk for internal organ involvement and variation in the extent of skin disease. Systemic sclerosis can be diffuse or limited. Limited systemic sclerosis is also called CREST (calcinosis, Raynaud's esophageal dysfunction, sclerodaytyl), telangiectasiae). Scleroderma-like disorders are believed to be related to industrial environment exposure. In Sine disease, there is internal organ involvement without skin changes.

The major manifestations of scleroderma and in particular of systemic sclerosis are inappropriate excessive collagen synthesis and deposition, endothelial dysfunction, spasm, collapse and obliteration by fibrosis.

Scleroderma is a rare disease with a stable incidence of approximately 19 cases per 1 million persons. The cause of scleroderma is unknown. However, the genetic predisposition is important. Abnormalities involve autoimmunity and alteration of endothelial cell and fibroblast function. Indeed, systemic sclerosis is probably the most severe of the auto-immune diseases with 50% mortality within 5 years of diagnosis (Silman, 1991).

In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

Several underlying biological processes are implicated in the initiation, severity and progression of the disease and include vascular dysfunction, endothelial cell activation and damage, leukocyte accumulation, auto-antibody production and crucially, an uncontrolled fibrotic response which may lead to death (Clements and Furst, 1996). Fibroblasts have a pivotal role in the pathogenesis of this disease. Primary fibroblasts obtained from patients with scleroderma exhibit many of the characteristic properties of the disease seen in vivo, notably increased extracellular matrix synthesis and deposition, notably of collagen and fibronectin, and altered growth factor and cytokine production such as of TGFβ and CTGF (Strehlow and Korn, 1998 and LeRoy, 1974).

There is no curative treatment of scleroderma. Innovative but high-risk therapy proposed autologous stem cell transplantation (Martini et al., 1999). In particular, there are currently no treatments for scleroderma targeting the fibrotic process (Wigley and Boling, 2000).

Identification of the genes associated with disease risk and scleroderma progression may lead to the development of effective strategies for intervention at various stages of the disease.

SARP-1 (secreted apoptosis-related protein 1) is a member of a family of secreted proteins known as secreted frizzled related proteins, based on their homology to the cysteine rich domain (CRD domain) found in the frizzled family of 7 transmembrane receptors (Rattner et al., 1997). Frizzled genes were originally identified in *drosophila* and control tissue polarity (Adler et al., 1987). Frizzled proteins are the receptors for the highly conserved Wnt family of at least 16 secreted signaling molecules that regulate cell-to-cell interactions during embryogenesis (Smalley and Dale, 1999). Insights into the mechanisms of Wnt action have emerged from several systems: genetics in *Drosophila* and *C. elegans*; biochemistry in cell culture; and ectopic gene expression in *Xenopus* embryos. Many Wnt genes in the mouse have been mutated, leading to very specific developmental defects. The Wnt signalling pathway which is triggered by the interaction of Wnt with frizzled proteins, is mediated through several cytoplasmic relay components, and functions to suppress the activity of the multiprotein β-catenin turnover complex, thus allowing a build up of cytosolic β-catenin which then enters the nucleus and forms a complex with TCF to activate transcription of Wnt target genes (Miller et al., 1999; Kuhl et al., 2000).

Wnt-frizzled interactions may be modulated through the restricted expression of distinct Wnt binding proteins, the secreted frizzled related proteins (sFRP). SFRPs are able to bind Wnt through the N-terminal CRD domain. They can therefore sequester Wnt away from its receptors and thereby antagonize its effects (Bafico et al., 1999).

SARP-1 is known under several alternative names, such as SDF-5, PRO697, ATG-1622, HLHDY31, SFRP-2. Partial or full length protein and/or nucleic acid sequences of murine or human SARP-1 have been described in several patent applications, e.g. WO 98/35043, WO 98/13493, EP 0 879 887, WO 99/46281.

In terms of function, the secreted frizzled-related proteins (SFRPs) appear to act as soluble modulators of Wnt signaling by competing with membrane-bound frizzled receptors for the binding of secreted Wnt ligands. Apart from SARP-1, the human proteins of this family so far known comprise SARP-2 (SFRP-1) and SARP-3 (SFRP-5). Murine SARP-1, and human SARPs-2 and -3 have been described to have the ability to either sensitize cells to apoptosis or to inhibit the apoptotic response (Melkonyan et al., 1997). When expressed in a breast adenocarcinoma cell line, mouse SARP-1 and human SARP-2 exhibited opposite effects on cell sensitivity to pro-apoptotic stimuli. Whereas cells with SARP-1 had higher resistance, cells expressing SARP-2 were sensitized to apoptosis induced by tumor necrosis factor and ceramide. Expression of SARP-1 or SARP-2 modified the intracellular levels of β-catenin, an indicator of Wnt mediated signal transduction, suggesting that SARPs interfere with the Wnt-frizzled signaling pathway (Melkonyan et al., 1997).

Northern blot analysis revealed that the SARP genes have distinct expression patterns (Leimeister et al., 1998). SARP-1 exists as 2.2- and 1.3-kb transcripts in several human tissues, with the highest levels in colon and small intestine. Chang et al., 1999, reported that SARP-1, or SFRP-2, is highly and preferentially expressed in bovine retina throughout the inner nuclear layer. Within the retina, SARP-3, or SFRP-5, is specifically expressed in the retinal pigment epithelium.

By analysis of somatic cell hybrids, Melkonyan et al. (1997) mapped the SARP-1 gene to human chromosome 4. Chang et al. (1999) refined the map position to 4q31.3 using radiation hybrid analysis.

There is also mounting evidence that an altered SARP-1 expression is related to cancer (WO 98/13493).

SUMMARY OF THE INVENTION

The invention is based on the finding of a beneficial effect of SARP-1 in an established animal model of scleroderma.

It is therefore a first object of the invention to use SARP-1 for the preparation of a medicament for the treatment and/or prevention of scleroderma, and in particular of systemic sclerosis. It is a second object of the invention to use a cell expressing SARP-1 or an expression vector comprising the coding sequence of SARP-1 for the preparation of a medicament for the treatment and/or prevention of scleroderma, in particular systemic sclerosis. Pharmaceutical compositions comprising SARP-1 and methods of treatment comprising administering SARP-1 to the human body are also within the scope of the present invention.

BRIEF DESCRIPTION OF THE DRAWINGS

FIG. 5 A and B are contiguous and show the nucleotide sequence (SEQ ID NO:1) and deduced amino acid sequence (SEQ ID NO:2) of SARP-1 cDNA. The predicted cleavage positions for the signal peptide are indicated by arrows.

FIG. 6 shows the alignment of human (SEQ ID NO:2) and murine (SEQ ID NO:5) SARP-1 amino acid sequences. Non-identical residues between the two sequences are highlighted (gray).

DESCRIPTION OF THE INVENTION

Figure 1:
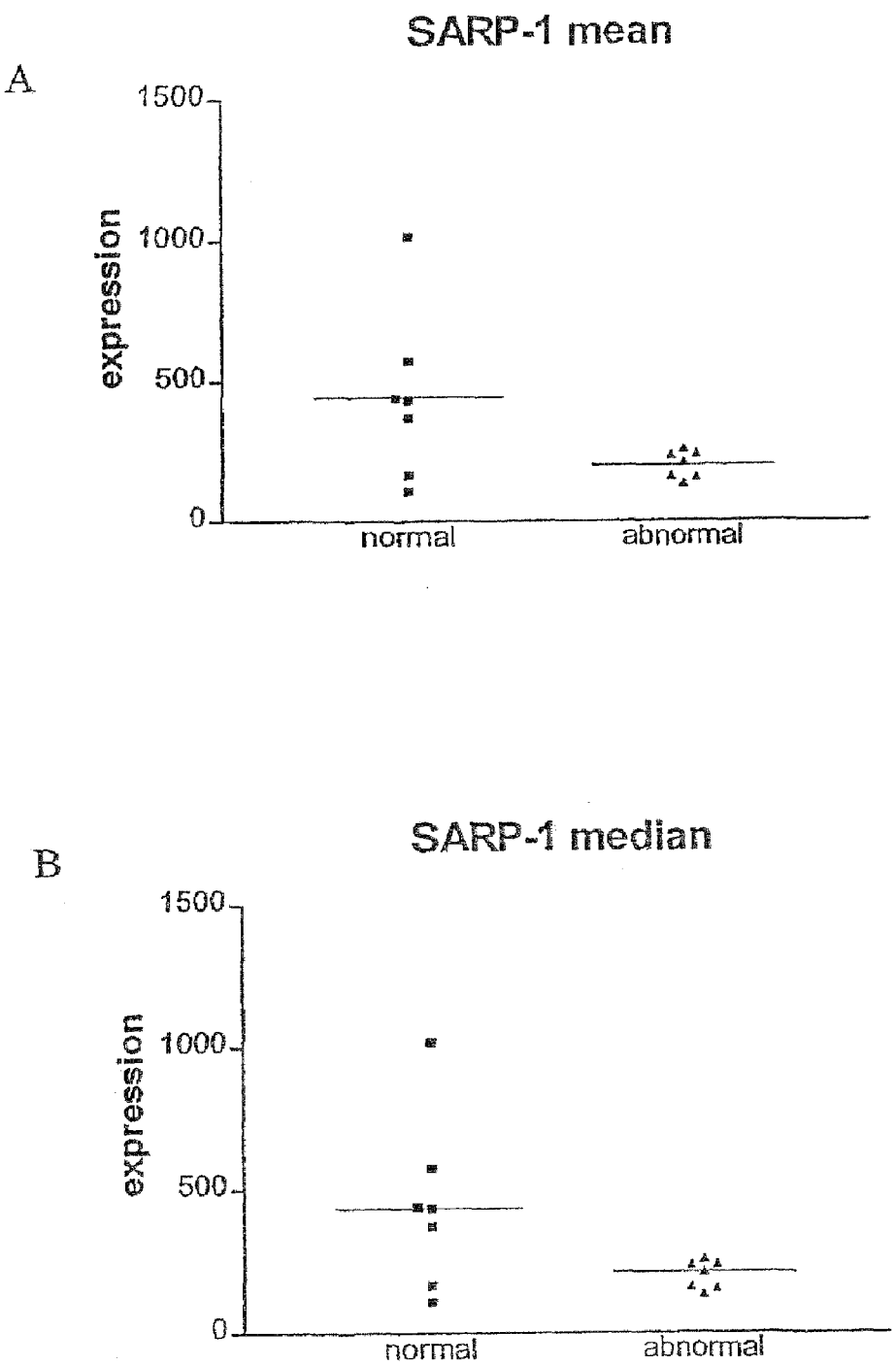
FIG. 1 shows the expression of SARP-1 mRNA in normal and diseased fibroblasts from 7 scleroderma patients as determined by gene filter analysis. The mean expression level for each class of samples (normal or abnormal) is given in (A) and the median is given in (B).

In accordance with the present invention it has been found that expression of the secreted protein SARP-1 is significantly lower in diseased fibroblasts derived from scleroderma patients as compared to control cells. DNA gene filter microarray technology has been used to identify differentially expressed genes in skin fibroblasts isolated from fibrotic lesions obtained from patients with scleroderma compared to fibroblasts isolated from clinically unaffected areas of the skin from the same patients. The expression of SARP-1 was down regulated in the lesional fibroblasts in 5 out of 7 patients tested. In addition to this, real time RT-PCR analysis of total RNA isolated from whole biopsy specimens of abnormal skin from scleroderma patients indicated lower levels of SARP-1 mRNA compared to clinically normal, age, sex and anatomical site matched control biopsies.

In support of the above results, a statistical method comparing expression levels of all of the genes contained on the gene filter microarray indicated that the downregulation of SARP-1 had a 95% probability of being associated with the fibrotic lesions in the patients, suggesting an association with the clinical progression of the disease.

The beneficial effect of SARP-1 in scleroderma was confirmed in a well-established murine model of scleroderma, the bleomycin-induced lung fibrosis model. In this model, administration of SARP-1 expressing cells reduced significantly the proportion of lung fibrosis.

Therefore, the invention relates to the use of a substance which binds to and initiates signaling of the human SARP-1 receptor or a substance which stimulates release or potentiates the activity of endogenous SARP-1 for the manufacture of a medicament for the treatment and/or prevention of scleroderma. Said substance may be mature SARP-1 itself or any fragment of SARP-1 binding to and initiating signaling through the SARP-1 receptor, as well as any further agonist of the SARP-1 receptor, such as agonistic antibodies directed to the SARP-1 receptor or chemical agonists specific therefor.

A receptor which has been suggested for SARP-1 is the wnt-protein, putatively binding to the cysteine rich frizzled (frz) domain of SARP-1 (Lin et al., 1997). The substance according to the invention may therefore also be a fragment of SARP-1 comprising the cysteine rich frizzled domain thereof.

Preferably, the substance used for treatment and/or prevention of scleroderma is selected from the group consisting of:
(a) Mature SARP-1;
(b) A polypeptide comprising SEQ ID NO: 2;
(c) A polypeptide comprising amino acids 21 to 295 of SEQ ID NO: 2;
(d) A polypeptide comprising amino acids 24 to 295 of SEQ ID NO: 2;
(e) A polypeptide comprising amino acids 25 to 295 of SEQ ID NO: 2;
(f) A polypeptide comprising amino acids 26 to 295 of SEQ ID NO: 2;

(g) A polypeptide comprising amino acids 27 to 295 of SEQ ID NO: 2;

(h) A polypeptide comprising amino acids 28 to 295 of SEQ ID NO: 2;

(i) A polypeptide comprising amino acids 37 to 295 of SEQ ID NO: 2;

(j) A mutein of any of (a) to (i), wherein the amino acid sequence has at least 40% or 50% or 60% or 70% or 80% or 90% identity to at least one of the sequences in (a) to (i);

(k) A mutein of any of (a) to (i) which is encoded by a DNA sequence which hybridizes to the complement of the native DNA sequence encoding any of (a) to (i) under moderately stringent conditions or under high stringent conditions;

(l) A mutein of any of (a) to (i) wherein any changes in the amino acid sequence are conservative amino acid substitutions to the amino acid sequences in (a) to (i);

(m) a salt or an isoform, fused protein, functional derivative, active fraction or circularly permutated derivative of any of (a) to (l).

The full length cDNA of human SARP-1 has been cloned and is depicted in FIG. 5 as well as SEQ ID NO: 1 of the attached sequence listing. The corresponding amino acid sequence is given in FIG. 5 and SEQ ID NO: 2 of the attached sequence listing. As shown in the examples below, it has been found that the N-terminus of SARP-1 is highly heterologous. The signal peptide of SARP-1 has been predicted to span either from amino acids 25 to 295 of SEQ ID NO: 2 or from amino acids 21 to 295. N-terminal sequences of purified recombinant human SARP-1 expressed in HEK 293 cells has revealed further N-terminal sequences leading of mature SARP-1 beginning at amino acids 24, 25, 26, 27, 28 or 37 of SEQ ID NO: 2.

The term "SARP-1", as used herein, relates to any or all of the substances considered above in (a) to (m).

The term "treatment and/or prevention" as used herein encompasses any attenuation, reduction, or partial, substantial or complete prevention or blockage of disease formation, development, progression or of the formation, development or progression of any one or several or all of the symptoms of the disease.

The term "scleroderma" as used herein comprises scleroderma in any classification and definition, as well as one or more of the symptoms of scleroderma, as described in detail in the introduction. The term "scleroderma" further relates to the diseases known to be associated with scleroderma, such as the ones described in Smith (2000), for example, which is fully incorporated by reference herein.

The term "scieroderma" as used herein comprises further fibrotic diseases such as liver cirrhosis, interstitial pulmonary fibrosis, Dupuytren's contracture, keloid and other scarring/wound healing abnormalities, postoperative adhesions and reactive fibrosis, as well as chronic heart failure, in particular after myocardial infarction. The invention relates to the use of SARP-1 for the manufacture of a medicament for the treatment and/or prevention of fibrotic diseases, such as the ones listed above.

Further diseases or disorders treatable with SAPR-1 comprise wound healing diseases, in particular wound healing in the lung, comprising chronic inflammation of the lung and ultimately fibrosis or scarring of lung surfaces. Disorders involving inflammation of the lung comprise e.g. idiopathic pulmonary fibrosis, sarcoidosis, bronchopulmonary dysplasia, fibroproliferative ARDS, as well as pulmonary manifestations or systemic diseases such as rheumatoid arthritis (Krein et al., 2001).

The term "scleroderma" preferably relates to localized, systemic, limited and diffuse scleroderma as well as overlap syndromes.

Localized scleroderma primarily affects the skin, but may also affect the underlying muscles and bones. However, it does not affect internal organs. Localized scleroderma is relatively mild, and may be related to systemic scleroderma in terms of similar superficial symptoms, such as the appearance of skin biopsy under the microscope.

Systemic scleroderma comprises several types of symptoms or groups of symptoms, such as CREST, limited and diffuse. Systemic scleroderma is also known as systemic sclerosis. It may also be referred to as progressive systemic sclerosis, or familial progressive systemic sclerosis. Systemic scleroderma may e.g. affect the skin, blood vessels, and/or internal organs. When it affects the skin, it can cause the skin to harden, most commonly on the hands and/or face. When it affects the blood vessels, it can cause Raynaud's disease. The most serious forms of systemic sclerosis affect the internal organs, and may cause disability or even death. Among others, systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system. With regard to the nervous system abnormalities, carpal tunnel syndrome followed by trigeminal neuralgia are the most common.

Limited Scleroderma may be limited to the hands, although the face and neck may also be involved.

Diffuse Scleroderma comprises skin tightening and also occurs above the wrists (or elbows). There are several subcategories of diffuse systemic sclerosis, such as "scleroderma sine scleroderma" where there is internal organ fibrosis, but no skin tightening; and familial progressive systemic sclerosis, a rare form which occurs in families.

Overlap syndromes are referred to if a scleroderma patient also has other autoimmune disease (such as lupus, rheumatoid arthritis, etc.), as e.g. in diffuse scleroderma in overlap with lupus. Scleroderma symptoms can also be a part of mixed connective tissue disease (MCTD), or Undifferentiated Connective Tissue Disease (UCTD).

The term "SARP-1" as used herein, relates to a protein comprising all or a portion of the sequence of SEQ ID NO: 2 (human) or SEQ ID NO: 5 (murine) of the enclosed sequence listing, irrespective of the designation of such protein, including, but not limited to the further known designations SDF-5, PRO697, ATG-1622, HLHDY31, SFRP-2 or FRP-2, as well as to salts, isoforms, muteins, active fractions, functional derivatives and circularly permutated derivatives thereof.

Preferably, the term "SARP-1" refers to a mature protein lacking the signal peptide. The signal peptide is predicted to contain the first 20 or the first 23, 24, 25, 26, 27 or 36 amino acids of SAPP-1 as defined in SEQ ID NO: 2, meaning that the mature protein would either comprise amino acids 21 to 295 or 24, 25, 26, 27, 28 or 37 to 295 of SEQ ID NO: 2.

As shown in FIG. 6 below, the human amino acid sequence of SARP-1 is highly homologous to the murine sequence (SEQ ID NO: 5). Therefore, murine SARP-1 may also be used according to the invention, as well as proteins derived from other species, as long as there is a sufficiently high identity between the proteins as to allow the protein to exhibit its biological activity, and without eliciting a substantial immune response in a human being.

The term "SARP-1" further relates to any fragment, portion, domain or sub-domain of SEQ ID NO: 2 or 5 showing the desired activity in scleroderma. Protein fragments or one or more domains of the protein may be used according to the invention, as long as they exhibit any beneficial effect on scleroderma, preferable an effect which is at least comparable of the full length protein. The beneficial effect can be measured in one of the in vitro or in vivo tests described in the examples below, or in any other assay adequate to demonstrate an effect in scleroderma. For example, SARP-1 comprises a cysteine rich frizzled domain, and a netrin-like domain, also called NTR module, which is homologous to tissue inhibitors of metalloproteinases (TIMPs) (Banyai and Patthy, 1999). Therefore, a fragment comprising the frizzled domain of SARP-1, or a fragment comprising the NTR module are preferred fragments according to the invention.

In accordance with the present invention, SARP-1 can be a naturally occurring, i.e. native protein, or a recombinant protein. Recombinant production may be carried out in eukaryotic cells, such as yeast cells or CHO cells, in human fibroblast cells or cell lines. It may further be produced in prokaryotic cells such as E. coli.

Preferably, SARP-1 is glycosylated at one or more sites. It may also be unglycosylated, depending on the given needs and the source of production or isolation of the protein.

The term "salts" herein refers to both salts of carboxyl groups and to acid addition salts of amino groups of SARP-1 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of SARP-1 relevant to the present invention, i.e., exert a beneficial effect on scleroderma.

Isoforms or splice variants of SARP-1 may also be used according to the invention, as long as they are capable of inhibiting scleroderma disease progression and/or symptoms of that disease. The two 1.3 kb and 2.2 kb transcripts found to be differentially expressed in human tissues may for instance represent different isoforms of SARP-1, which could be useful according to the invention.

As used herein the term "muteins" refers to analogs of an SARP-1, in which one or more of the amino acid residues of a natural SARP-1 are replaced by different amino acid residues, or are deleted, or one or more amino acid residues are added to the natural sequence of SARP-1, having preferably at least the same activity as wild type SARP-1 or even having a much more potent activity. These muteins are prepared by known synthesis and/or by site-directed mutagenesis techniques, or any other known technique suitable therefor.

Any such mutein preferably has a sequence of amino acids sufficiently duplicative of that of SARP-1, as described in SEQ ID NO: 2, such as to have at least a substantially similar activity of SARP-1. The activity of a SARP-1 mutant can be tested by assays know n in the art, and in particular using the assays explained in the examples below. Measuring the amount of collagen synthesis (example 7) in fibroblasts is a suitable test for assessing the activity of SARP-1 muteins, for example.

Muteins in accordance with the present invention include proteins encoded by a nucleic acid, such as DNA or RNA, which hybridizes to DNA or RNA, which encodes SARP-1, in accordance with the present invention, under stringent conditions. The term "stringent conditions" refers to hybridization and subsequent washing conditions, which those of ordinary skill in the art conventionally refer to as "stringent".

See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of SARP-1, such as to have substantially similar, or even better, biological activity as SARP-1.

One easily measurable activity of SARP-1 is its capability of reducing collagen synthesis. An assay for measuring this activity is described in detail in example 6 below. As long as the mutein has substantial collagen reducing activity, it can be considered to have substantially similar activity to SARP-1. Thus, it can be determined whether any given mutein has at least substantially the same activity as SARP-1 by means of routine experimentation comprising subjecting such a mutein, e.g., to a simple assay as described in example 7.

In a preferred embodiment, any such mutein has at least 40% identity or homology with the sequence of SEQ ID NO: 2 of the annexed sequence listing. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nim.nih.gov) and FASTA (Pearson W R, 1990; Pearson 1988).

Muteins of SARP-1, which can be used in accordance with the present invention, or nucleic acids coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of SARP-1 polypeptides or proteins, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of SARP-1 polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising SARP-1, or a mutein thereof, fused with another protein, which, e.g., has an extended residence time in body fluids. Fusion proteins comprising all or a functional part of SARP-1 fused to all or a functional part of a protein capable of improving the biological activities of the molecule, like half-life in the human body, for instance, are preferred according to the invention. In a preferred embodiment the fused protein comprises an immunoglobulin (Ig) fusion. Fusion proteins comprising all or part of SARP-1 fused to all or part of an immunoglobulin are highly preferred. They can be monomeric or multimeric, hetero- or homomultimeric. Advantageously, the fused protein comprises the constant region of an immunoglobulin, in particular of the Fc portion of the immunoglobulin. Embodiments in which the immunoglobulin is of the IgG1 or IgG2 isotype are further preferred according to the invention.

SARP-1 may thus be fused to another protein, polypeptide or the like, e.g., an immunoglobulin or a fragment thereof. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:6) introduced between the SARP-1 sequence and the immunoglobulin sequence.

"Functional derivatives" as used herein cover derivatives of SARP-1, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is at least substantially similar to the activity of SARP-1, and do not confer toxic properties on compositions containing it. Therefore, in a preferred embodiment the functional derivative comprises at least one moiety attached to one or more functional groups which occur as one or more side chains on the amino acid residues.

In accordance with the present invention, polyethylene glycol (PEG) side-chains are highly preferred moieties. PEG side chains may mask antigenic sites and extend the residence of the substance they are attached to in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

"Active fractions" of SARP-1 and its muteins and fused proteins, cover any fragment or precursors of the polypeptide chain of the protein molecule alone or together with associated molecules or residues linked thereto, e.g., sugar or phosphate residues, or aggregates of the protein molecule or the sugar residues by themselves, provided said active fraction has at least a substantially similar activity to SARP-1.

The invention further relates to the use of a nucleic acid molecule for manufacture of a medicament for the treatment and/or prevention of scleroderma, wherein the nucleic acid molecule comprises a nucleic acid sequence encoding a polypeptide comprising an amino acid sequence selected from the group consisting of:

(a) Mature SARP-1;
(b) A polypeptide comprising SEQ ID NO: 2;
(c) A polypeptide comprising amino acids 21 to 295 of SEQ ID NO: 2;
(d) A polypeptide comprising amino acids 24 to 295 of SEQ ID NO: 2;
(e) A polypeptide comprising amino acids 25 to 295 of SEQ ID NO: 2;
(f) A polypeptide comprising amino acids 26 to 295 of SEQ ID NO: 2;
(g) A polypeptide comprising amino acids 27 to 295 of SEQ ID NO: 2;
(h) A polypeptide comprising amino acids 28 to 295 of SEQ ID NO: 2;
(i) A polypeptide comprising amino acids 37 to 295 of SEQ ID NO: 2;
(j) A mutein of any of (a) to (i), wherein the amino acid sequence has at least 40% or 50% or 60% or 70% or 80% or 90% identity to at least one of the sequences in (a) to (i);
(k) A mutein of any of (a) to (i) which is encoded by a DNA sequence which hybridizes to the complement of the native DNA sequence encoding any of (a) to (i) under moderately stringent conditions or under high stringent conditions;
(l) A mutein of any of (a) to (i) wherein any changes in the amino acid sequence are conservative amino acid substitutions to the amino acid sequences in (a) to (i);
(m) a salt or an isoform, fused protein, functional derivative, active fraction or circularly permutated derivative of any of (a) to (l)

for the manufacture of a medicament for the treatment and/or prevention of scleroderma. The invention equally relates to the use of said nucleic acid molecules for the treatment and/or prevention of scleroderma.

In accordance with the present invention, SARP-1 may also be administered to the human body in form of a vector comprising said nucleic acid molecule. Therefore, the invention further relates to the use of a vector comprising said nucleic acid molecule for the manufacture of a medicament for the treatment and/or prevention of scleroderma. Preferably, the vector is an expression vector, comprising a promoter operably linked to all or part of the coding sequence of SARP-1. In a further preferred embodiment, the vector is a gene therapy vector. Gene therapy vectors are known in the art, most of them are virally derived vectors, such as adenoviral or lentiviral vectors.

According to the invention, SARP-1 may also be administered to the human body in form of a cell producing and/or secreting SARP-1. Therefore, the invention further relates to the use of a cell expressing SARP-1 for the manufacture of a medicament for the treatment and/or prevention of scleroderma, i.e. to cell therapy for the treatment and/or prevention of scleroderma. The cell may be a naturally producing SARP-1 and/or a transfected cell that produces recombinant SARP-1. Preferred are cells expressing and secreting high amounts of the protein, such as over-expressing cells carrying high copy numbers of an expression vector comprising a nucleic acid molecule encoding SARP-1.

As fibroblasts represent the machinery of fibrosis they are the most suitable cells for anti-fibrotic and scleroderma therapy. Therefore, preferably, SARP-1 expressing fibroblasts are used in accordance with the present invention.

The invention further relates to a cell comprising a vector comprising a nucleic acid molecule encoding all or part of SARP-1 for the preparation of a medicament for treatment and/or prevention of scleroderma. A cell that has been genetically modified to produce a polypeptide according to the invention is also within the scope of the present invention.

The use of an expression vector for inducing and/or enhancing the endogenous production of SARP-1 in a cell normally silent or expressing amounts of the inhibitor which are not sufficient, are also contemplated according to the invention. Thus, the invention makes use of a technology known as endogenous gene activation (EGA) for the production of the desired protein.

Systemic sclerosis is one of the most serious diseases within scleroderma, often leading to disablement and death. Therefore, a further preferred embodiment of the invention relates to systemic sclerosis, which is an indication within the disease of scleroderma, being characterized mainly by involvement of internal organs, as described in detail above.

Several combination treatments are preferred in accordance with the present invention. Therefore, preferably, the medicament of the invention further comprises:

Interferon, in particular interferon-β

A Tumor Necrosis Factor (TNF) antagonist, in particular TBPI and/or TBP II

A further anti-scleroderma agent

An anti-scleroderma agent selected from the group consisting of ACE inhibitors, calcium channel blockers, proton pump inhibitors, NSAIDs, COX-inhibitors, corticosteroids, tetracycline, pentoxifylline, bucillamine, geranylgeranyl transferase inhibitors, rotterlin, prolyl-4-hydroxlase inhibitors, c-proteinase inhibitors, lysyl-oxidase inhibitors, relaxin, halofuginone, prostaglandins, prostacyclins, endothelin-1, nitric oxide, angiotensin II inhibitors and anti-oxidants.

All treatments are intended for simultaneous, sequential or separate use.

Although there is presently no cure for scleroderma, several agents or treatments are presently being used to treat scleroderma symptoms. Such anti-scleroderma agents, which may be used as combination therapy according to the invention, are summarized e.g. in Leighton (2001) or Wigley and Sule (2001), which are fully incorporated by reference herein.

Interferons are predominantly known for inhibitory effects on viral replication and cellular proliferation. Interferon-γ, for example, plays an important role in promoting immune and inflammatory responses. Interferon β (IFN-β, an interferon type 1), is said to play an anti-inflammatory role.

In yet a further embodiment of the invention, SARP-1 is used in combination with a TNF antagonist. TNF antagonists exert their activity in several ways. First, antagonists can bind to or sequester the TNF molecule itself with sufficient affinity and specificity to partially or substantially neutralise the TNF epitope or epitopes responsible for TNF receptor binding (hereinafter termed "sequestering antagonists"). A sequestering antagonist may be, for example, an antibody directed against TNF.

Alternatively, TNF antagonists can inhibit the TNF signalling pathway activated by the cell surface receptor after TNF binding (hereinafter termed "signalling antagonists"). TNF antagonists are easily identified and evaluated by routine screening of candidates for their effect on the activity of native TNF on susceptible cell lines in vitro, for example human B cells, in which TNF causes proliferation and immunoglobulin secretion. The assay contains TNF formulation at varying dilutions of candidate antagonist, e.g. from 0.1 to 100 times the molar amount of TNF used in the assay, and controls with no TNF or only antagonist (Tucci et al., 1992).

Sequestering antagonists are the preferred TNF antagonists to be used according to the present invention. Amongst sequestering antagonists, those polypeptides that bind TNF with high affinity and possess low immunogenicity are preferred. Soluble TNF receptor molecules and neutralising antibodies to TNF are particularly preferred. For example, soluble forms of TNF-RI (p55) and TNF-RII (p75) are useful in the present invention. Truncated forms of these receptors, comprising the extracellular domains of the receptors or functional portions thereof, are more particularly preferred antagonists according to the present invention. Truncated soluble TNF type-I and type-II receptors are described in EP914431, for example.

Truncated forms of the TNF receptors are soluble and have been detected in urine and serum as about 30 kDa or 40 kDa TNF inhibitory binding proteins, which are called TBPI and TBPII, respectively (Engelmann et al., 1990). The simultaneous, sequential, or separate use of SARP-1 with the TNF antagonist and/or an Interferon is preferred, according to the invention.

According to the invention, TBPI and TBPII are preferred TNF antagonists to be used in combination with an SARP-1. Derivatives, fragments, regions and biologically active portions of the receptor molecules functionally resemble the receptor molecules that can also be used in the present invention. Such biologically active equivalent or derivative of the receptor molecule refers to the portion of the polypeptide, or of the sequence encoding the receptor molecule, that is of sufficient size and able to bind TNF with such an affinity that the interaction with the membrane-bound TNF receptor is inhibited or blocked.

In a further preferred embodiment, human soluble TNF-RI (TBPI) is the TNF antagonist to be used according to the invention. The natural and recombinant soluble TNF receptor molecules and methods of their production have been described in the European Patents EP 308 378, EP 398 327 and EP 433 900.

Whilst it may be beneficial to block TNF-α in early stages of the disease, it has been discussed that in later stages, TNF itself may exert a beneficial effect on scleroderma (Abraham et al., 2000). Therefore, the invention further relates to a combination of SARP-1 and TNF-α for treatment or prevention of scleroderma, in particular in advanced stages of disease.

COX inhibitors are known in the art. Specific COX-2 inhibitors are disclosed in WO 01/00229, for example.

The invention further relates to a pharmaceutical composition comprising SARP-1, optionally together with one or more pharmaceutically acceptable carriers, diluents or excipients, for the treatment and/or prevention of scleroderma, in particular systemic sclerosis. The pharmaceutical composition may further comprise any of the above-identified further components, and in particular an interferon, a TBP or a COX inhibitor.

The pharmaceutical composition according to the invention may also comprise a vector comprising a nucleic acid molecule according to the invention, or a cell expressing SARP-1.

The active ingredients of the pharmaceutical, i.e. polypeptides, nucleic acids or cells according to the invention, or combinations thereof, as well as the combinations of substances mentioned above, may be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector) which causes the active agent to be expressed and secreted in vivo. In addition, the protein(s) according to the invention can be administered together with other components of biologically active agents such as pharmaceutically acceptable surfactants, excipients, carriers, diluents and vehicles.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringers solution.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amount of the active protein (s) will be a function of many variables, including the type of receptor, the affinity of the substance according to the invention to its receptor, any residual cytotoxic activity exhibited thereby, the route of administration, the clinical condition of the patient.

A "therapeutically effective amount" is such that when administered, the substance according to the invention results in activating the SARP-1 receptor, or inactivating a ligand stimulating the receptor in vivo. The dosage administered, as single or multiple doses, to an individual will vary depending upon a variety of factors, including SARP-1 pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art.

The dose of the polypeptide according to the invention required will vary from about 0.0001 to 100 mg/kg or about 0.01 to 10 mg/kg or about 0.1 to 5 mg/kg or about 1 to 3 mg/kg, although as noted above this will be subject to a great deal of therapeutic discretion.

The daily doses are usually given in divided doses or in sustained release form effective to obtain the desired results. Second or subsequent administrations can be performed at a dosage, which is the same, less than or greater than the initial or previous dose administered to the individual. A second or subsequent administration can be administered during or prior to onset of the disease.

The invention further relates to a method for treating and/or preventing scleroderma, in particular systemic sclerosis, comprising administering to a patient in need thereof an effective amount of a polypeptide according to the invention, optionally together with a pharmaceutically acceptable carrier. Alternatively, or additionally, a cell producing SARP-1 or a nucleic acid molecule of the invention, optionally comprised in an expression vector, may be administered according to the invention.

The expression vector may be administered systemically. Preferably the expression vector is administered by intramuscular injection. A further preferred route of administration is inhalation, in particular if lung fibrosis is involved in the disease.

The invention further relates to a method for the preparation of a pharmaceutical composition comprising admixing an effective amount of SARP-1 with a pharmaceutically acceptable carrier, and to a method of treatment and/or prevention of arthritis comprising administering to a host in need thereof an effective inhibiting amount of SARP-1.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Example 1

SARP-1 is Differentially Expressed in Skin Fibroblasts from Scleroderma Patients Methods Patient Samples Two mm3 punch biopsies were taken from lesional or non-lesional skin (usually from forearm skin) of nine age and sex matched patients with diffuse cutaneous systemic sclerosis (SSc). All patients fulfilled the criteria of the American College of Rheumatology for the diagnosis of systemic sclerosis.

Fibroblast cultures.

Fibroblasts were obtained from the biopsies by in vitro culture as previously described (Abraham et al., 1991). Briefly, biopsies were cut into pieces and placed in sterile plastic dishes or flasks. After 15 minutes of drying at room temperature the pieces of biopsy were adherent to the tissue culture plastic and were then cultured in fibroblast growth medium (FGM) consisting of Dulbecco's modified Eagle's medium (DMEM) containing 10% fetal calf serum (FCS), 2 mM L-glutamine, 1 mM sodium pyruvate, 100 units per ml penicillin, 100 μg per ml streptomycin, 50 μg per ml gentamicin and 2.5 μg per ml amphotericin B. After 2-3 weeks of incubation in a humidified atmosphere of 5% $CO_2$ in air, the fibroblast outgrowths were detached by brief trypsin treatment and re-cultured in FGM without gentamicin and amphotericin B. In experiments, fibroblasts were used between passages 2 and 5. The fibroblast phenotype was confirmed by their typical morphology in monolayer and three-dimensional collagen gel cultures.

RNA Isolation

Total RNA was isolated from confluent scleroderma fibroblasts in early passage or from primary cultures (passage 1-3) of normal human dermal (foreskin) fibroblasts (purchased from Promocell) using Trizol (Life Technologies) according to the manufacturer's protocol. The final RNA pellet was resuspended in sterile DEPC treated water at a concentration of 1 µg/µl and stored at −80 C.

cDNA probe synthesis 2 µg total RNA was mixed with 1.3 µl of cytokine specific primers (R&D systems cat. no. GAC11) and incubated at 70 C for 2 min a 0.5 ml eppendorf tube. The tubes were then cooled to 50 C for 2 min after which time reaction mixture containing 2 µl of 5× reaction buffer (250 mM Tris-HCl pH 8.3, 375 mM KCl and 15 mM $MgCl_2$), 1 µl of 10× dNTP mixture (5 mM dGTP, 5 mM dCTP and 5 mM dTTP), 3.5 µl of α32P-dATP (3000 Ci/mmol, Amersham cat. no. PB10204), 0.5 µl DTT (100 mM) and 1 µl of Superscript II (Life Technologies) were added. The reaction mixture was mixed briefly by pipetting and incubated at 50 C for 25 min. The reaction was stopped by addition of 1 µl of 0.1 M EDTA pH 8.0 containing 1 mg/ml glycogen). The labelled cDNA was then purified from un-incorporated deoxynucleotides using a Chromaspin-200 DEPC-H20 column (Clontech) according to the manufacturer's instructions. cDNA containing fractions were identified by Czerenkov counting. The peak fraction (normally fraction 2 out of a total of 6 collected) was treated with 0.1 volumes of 1 M NaOH containing 1 mM EDTA for 20 min at 70 C to hydrolyze the RNA, and then neutralized with an equal volume of 1 M NaH2PO4 containing 2.5 µg of human Cot-1 DNA (Life Technologies) for 20 min at 70 C. The heat treated neutralized cDNA probe was then added directly to the hybridization mixture.

Hybridization to Gene Filter Microarrays

Gene filter microarrays (human cytokine expression array, R&D systems cat no. GA001) were prehybridized at 68 C for 2 h in 5 ml of Express Hybridization solution (Clontech) containing 0.5 µg/ml salmon sperm DNA (Life technologies) in roller bottles, in a Hybaid hybridization oven (MWG Biotech). After this time the prehybrization solution was replaced with fresh hybridization solution containing the cDNA probe preparation at a specific activity of between 0.25 to 1×106 cpm/ml. Hybridization was for 16-20 h at 68 C. After hybridization, filters were washed 4 times with 2×SSC/1% SDS at 68 C for 20 minutes per wash and twice with 0.1×SSC/0.5% SDS for 15 min per wash. Filters were then sealed in Saran wrap™ and exposed to a K-type storage phosphor imaging screen (Biorad) for varying times (4 h to 4 days) at room temperature.

Image Analysis

Imaging screens were scanned at a resolution of 50 µm using a Biorad Personal FX phosphoimager. The resultant 16 bit digital file was converted to TIF format and the image analyzed using Arrayvision software (Imaging Research Inc.). For each sample, we measured the pixel intensity of the 384 genes spotted in duplicate on the filter. The background signal was subtracted and an average pixel intensity for each pair of spots in the array was generated (=expression level).

Confirmation of microarray results on selected genes by RT-PCR.

1 µg of total RNA from each patient sample was reverse transcribed using an oligo dT primer (Promega) in a 20 µl reaction volume containing 5 mM $MgCl_2$, 10 mM Tris-HCl, 50 mM KCl, 0.1% Triton X-100, 1 mM each of dATP, dGTP, dCTP, dTTP, 0.5 units recombinant RNasin ribonuclease inhibitor (Promega) and 15 units AMV reverse transcriptase (Promega). The reaction mixture was incubated at 42 C for 60 min, heated at 95 C for 5 min then diluted to 200 µl with sterile water. Dilutions of the reverse transcriptase reaction were then subjected to real time PCR analysis on a Taqman (PE Applied Biosystems 7700) using specific primer pairs designed for each gene using Primer Express software (PE Applied Biosystems) based on the database accession number given by the gene filter manufacturer. Results were normalized to the expression of the housekeeping gene glyceraldehyde 3-phosphate dehydrogenase (GAPDH) in each sample and are expressed as fold changes, determined by dividing the expression value of the abnormal patient sample by the corresponding normal patient sample.

Statistical Method for Predicting Genes Associated with Scleroderma

The statistical method for predicting genes associated with scleroderma has been carried out by neighbor analysis and class predictor as described in detail in Golub et al., 1999, which is fully incorporated by reference herein.

Results

Gene filter microarray analysis was performed on normal and abnormal fibroblast samples from 7 scleroderma patients. The mean expression level of SARP-1 cDNA for each patient sample is shown in FIG. 1 A, the median expression is shown in FIG. 1 B. Mean and median values differ significantly between normal and abnormal cells, the normal expression level of SARP-1 being higher than the abnormal expression level. Medians are commonly used when dealing with patient samples as they minimize the effect of a widely variant individual within the group. Here, abnormal fibroblasts expressed significantly lower levels of SARP-1 mRNA compared to normal fibroblasts in 5 out of 7 patients tested.

Figure 2:
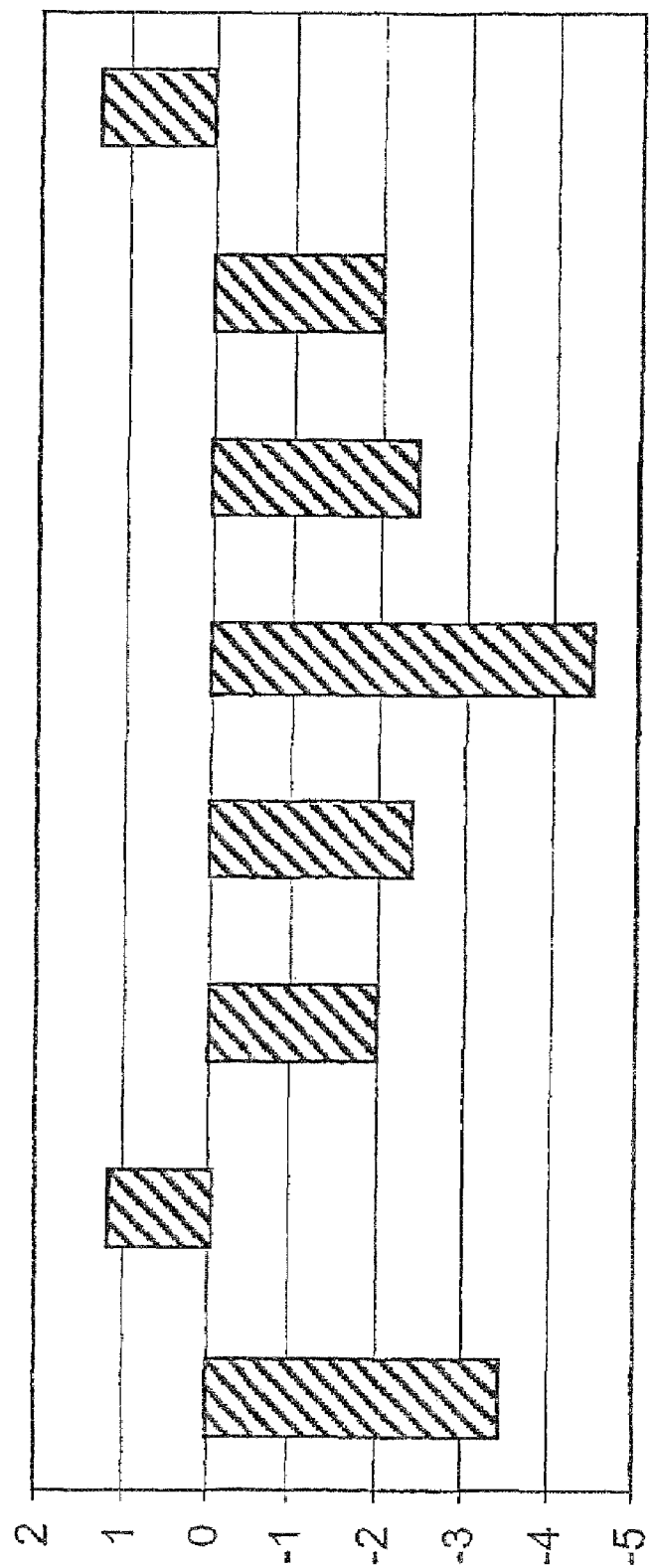
FIG. 2 shows the ratio of expression of SARP-1 mRNA in diseased/normal fibroblasts (low passage number, <5 passages) from 8 scleroderma patients determined by real time PCR.

The results obtained on the microarrays were further corroborated by real time PCR analysis of patient samples using SARP-1 specific PCR primers. Results are shown in FIG. 2 and are expressed as the fold change in expression level (abnormal divided by normal). In 6 out of the 8 patients tested, SARP-1 was down regulated at least 2 fold in diseased fibroblasts compared to normal fibroblasts taken from the same patient. In the 2 remaining patients the level of expression was comparable in normal and abnormal fibroblasts.

Figure 3:
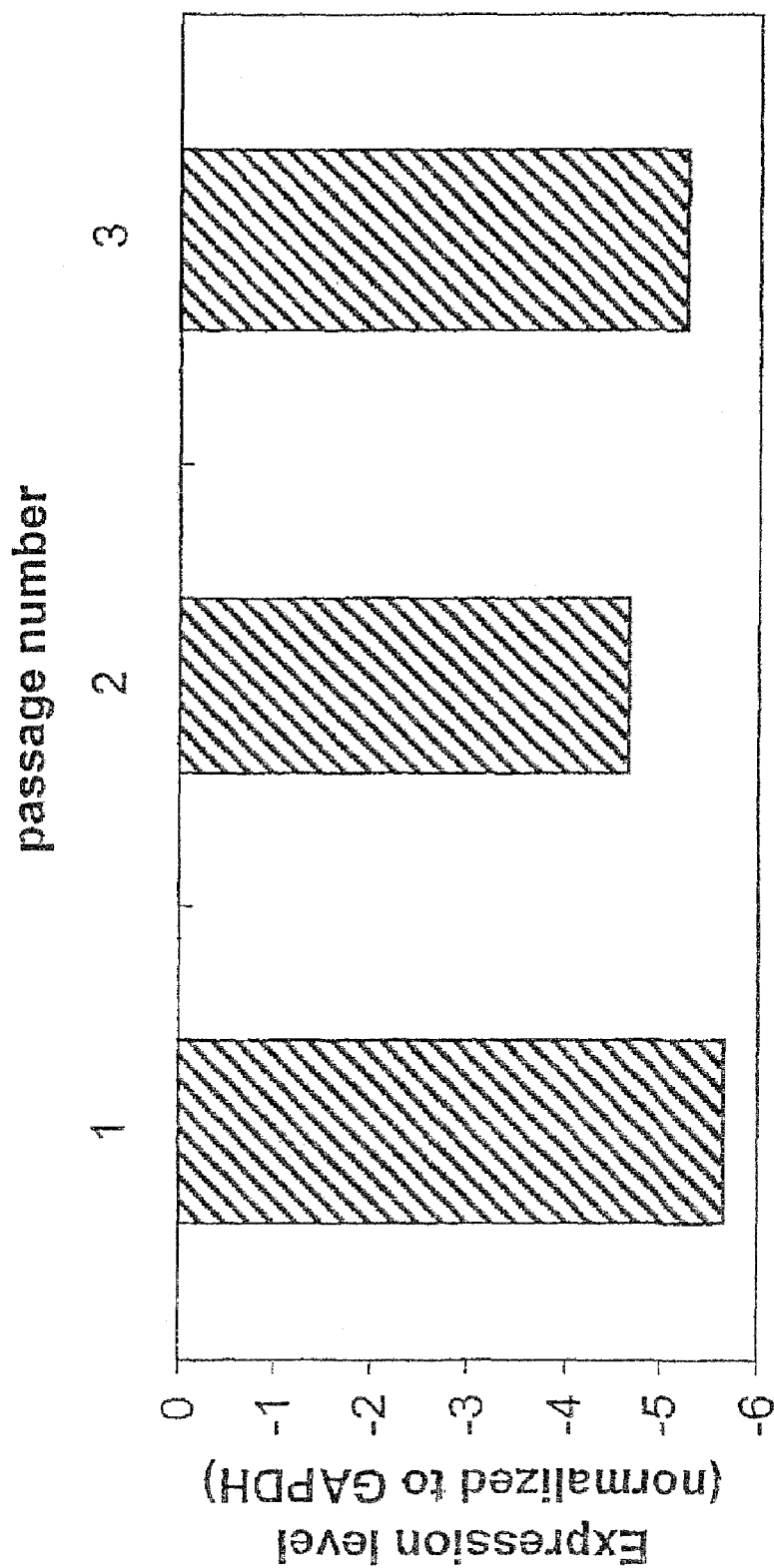
FIG. 3 shows the real time PCR analysis of SARP-1 mRNA expression in normal human dermal fibroblasts (NHDF) relative to GAPDH mRNA expression.
Figure 4:
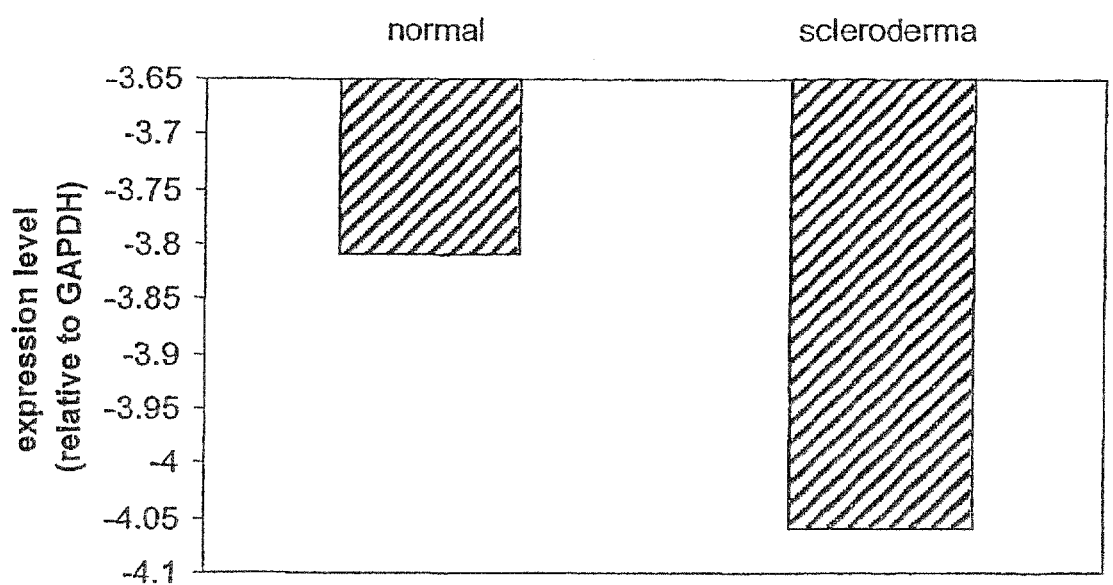
FIG. 4 shows real time PCR analysis of SARP-1 mRNA expression in clinically normal human skin biopsies (n=6) compared to abnormal skin biopsies from scleroderma patients (n=2) relative to GAPDH.

The differences in expression observed between normal and abnormal fibroblasts from the same patient are not due to differences in the culture conditions between the two populations since SARP-1 mRNA expression in primary cultures of normal human dermal fibroblasts does not change significantly on passaging the cells (FIG. 3). In addition real time RT-PCR analysis of total RNA isolated from whole biopsy specimens of abnormal skin from scleroderma patients indicated lower levels of SARP-1 mRNA compared to clinically normal, age, sex and anatomical site matched control biopsies (FIG. 4).

In addition to that, the downregulation of SARP-1 was shown to have a 95% probability of being associated with the progression of scleroderma using statistical methods.

Conclusion

The results described above show that there is a lack of SARP-1 in diseased tissue derived from scleroderma patients as compared to healthy tissue, indicating that restoring a normal level of SARP-1 may help curing the disease. Thus, SARP-1 may present a new medicine for achieving partial or full inhibition of the disease or of at least of one or more symptoms of scleroderma, or for inhibition of disease progression.

Example 2

Cloning of the Full cDNA Coding Sequence of Human SARP-1

Materials and Methods

Sequential BLAST searches were performed on the human dbEST (public EST database) starting with the partial coding sequence of SARP-1 (EMBL accession number: AF017986) and relevant ESTs were retrieved using ENTREZ at www.ncbi.nlm.gov/Web/Search/index.html. The following ESTs were then assembled along with the AF017986 sequence to generate the consensus full coding sequence of SARP-1: AW580647, AW608301, AA976403, and W92531.

The full length cDNA coding sequence of SARP-1 was then cloned by reverse transcriptase PCR using the following primers based on the consensus sequence obtained above: SARP-1F 5' GCC AAG CTT CCC ACG ATG CTG CAG GGC CCT (SEQ ID NO: 3) and SARP-1R 5' GCG CTC GAG CTA GCA CTG CAG CTT GCG GAT (SEQ ID NO: 4) at 50 pmole each in a 50 µl reaction mixture containing 0.3 mM dNTPs, 1 mM MgSO$_4$, 5 µl of normal human dermal (foreskin) fibroblast cDNA template (prepared as described above) 5 µl of 10× Pfx amplification buffer (Life Technologies) and 1 µl of Platinum Pfx DNA polymerase (Life Technologies). The reaction mixture was heated at 94 C for 2 min then subjected to 35 cycles of PCR as follows: 94 C 15 s, 55 C for 30 s and 68 C for 1 min. The amplification products were analyzed on 1% agarose gels in 1×TAE buffer (Life Technologies) and PCR products migrating at the predicted molecular mass (906 bp) were purified from the gel using the Wizard PCR purification kit (Promega).

100 ng of gel-purified DNA were digested with restriction enzymes HindIII and XhoI (Pharmacia), according to the manufacturer's conditions, re-purified as described above and ligated to HindIII/XhoI digested plasmid pcDNA3.1(+) (Invitrogen) using T4 DNA ligase (New England Biolabs) according to standard molecular biology techniques. Ligation products were transformed into E. coli strain TOP 10 F' (Invitrogen) by electroporation using a Biorad Gene Pulser. Plasmid DNA was isolated from 5 ml cultures grown up from the resultant colonies and subjected to automated sequence analysis on an Applied Biosystems 3700 sequencer using T7 and pcDNA3.1AS primers (Invitrogen) to confirm the sequence of SARP-1.

Results

In order to characterize SARP-1 activity in vitro and in vivo the full human cDNA coding sequence was cloned. The partial cDNA sequence of human SARP-1 (EMBL accession number AF017986) was used to identify overlapping ESTs in the dbEST public database using the BLAST program. The full cDNA coding sequence was assembled from the following sequence accession numbers: AF017986 AW580647, AW608301, AA976403, and W92531. The full-length DNA sequence and deduced amino acid sequence of SARP-1 are shown in FIGS. 5A and B (A and B should be read continuously). The cDNA coding sequence of SARP-1 was cloned by reverse transcriptase PCR using primers which flanked the predicted start and stop codons. Sequence analysis of the resultant SARP-1 cDNA clones revealed 93% identity at the nucleotide level to the published sequence of mouse SARP-1 (Melkonyan et al., 1997) and 95% identity to the mouse sequence at the amino acid level. The aligned human and mouse amino acid sequences of SARP-1 are depicted in FIG. 6. The predicted protein sequence is 295 amino acids with a predicted signal peptide of 20 or 24 amino acids using the SIGNALASE (Von Heijne, 1986) or SIGNALP programs respectively, see arrows in FIG. 5 A. The amino differences between the human and mouse sequences are highlighted in FIG. 6 and reside in the N-terminal signal peptide (4 amino acids) and in the mature protein sequence (2 amino acids).

SEQ ID NO: 1 of the enclosed sequence listing contains the coding strand of human SARP-1 cDNA and SEQ ID NO: 2 contains the amino acid sequence of human SARP-1. The murine amino acid sequence is illustrated in SEQ ID NO: 5 of the enclosed sequence listing.

Example 3

N-Terminal Sequence of Human SARP-1

The predicted SARP-1 signal peptide is 20 or 24 amino acids long (see FIG. 5A). In order to verify the correct N-terminus of mature SARP-1, recombinant SARP-1 containing a six residue histidine tag was expressed in HEK-293 cells and purified on a nickel-chelate column. The purified protein migrates as a 32 kDa band in SDS-PAGE, corresponding to the mass measured by MS, which was 34313 Da.

N-terminal sequences of the purified recombinant protein were obtained using an Applied Biosystems model 494 pulsed liquid phase protein sequencer with a model 148C on-line phenylthiohydantoin amino acid analyzer according to Maundrell et al. (1997). Briefly, purified SARP-1 was digested by overnight incubation at 37° C. in 90 µl of 100 mM Tris-HCl pH 8.5 containing 1 M urea, 20 mM methylamine, 1 mM dithiothreitol, and 5 µg of trypsin (Boehringer Mannheim, sequencing grade). Peptides were separated by reverse-phase HPLC (Hewlett Packard HP1090) with a Brownlee C18 column (220×2.1 mm). Peptides were eluted with an acetonitrile gradient (in 0.1% trifluoroacetic acid) from 0 to 55% over 60 min, followed by 55-70% over 5 min. Elution fractions were collected, and radioactive $^{33}$P-labeled phosphopeptides identified by scintillation spectrometry were sequenced by Edman degradation using an Applied Biosystems model 494 pulsed liquid phase protein sequencer with a model 148C on-line phenylthiohydantoin amino acid analyzer.

The sequence GLFLFGQPDFSYK (residues 24-36 of SEQ ID NO:2) was obtained by tandem mass spectrometry on a tryptic digest of the reduced and alkylated protein. Analyses were performed on a Q-TOF mass spectrometer (Micromass UK Limited, Manchester, UK) equipped with a Nano-Spray ion source essentially as described by Cavalli et al., 2001. Briefly, one microgram of the purified protein was resolved by 10% SDS-PAGE. The protein bands were excised from the silver-stained gel and digested in-gel with trypsin (Shevchenko et al., 1996). The extracted peptide mixture was analyzed by tandem mass spectrometric sequencing (Wilm et al., 1996) using a Q-TOF mass spectrometer (Micromass, Manchester, UK) equipped with a nano-electrospray ion source.

Results

The theoretical N-terminal sequence of immature SARP-1 is as follows:

```
       1        10        20        30        40
MLQGPGSLLL LFLASHCCLG SARGLFLFGQ PDFSYKRSNC KPIPANLQLC ...
(residues 1-50 of SEQ ID NO:2)
```

The position of the 2nd predicted signal cleavage site is between residue 24 and 25 (G and L).

In the sequencing experiments carried out, a considerable heterogeneity of the N-terminus of SARP-1 was found.

In one experiment, two major sequences were found, one starting with FGQPD (residues 28-32 of SEQ ID NO:2), i.e. starting at amino acid 28 of SEQ ID NO: 2, the other one starting with LFGQPD (residues 27-32 of SEQ ID NO:2), i.e. starting at amino acid 27 of SEQ ID NO: 2.

However, in addition in a different purified batch 4 sequences where found:

```
LFLFGQPDFS    (starts at amino acid 25)
              (residues 25-34 of SEQ ID NO:2)

FLFGQPDFS     (starts at amino acid 26)
              (residues 26-34 of SEQ ID NO:2)

LFGQPD.       (starts at amino acid 27)
              (residues 27-32 of SEQ ID NO:2)

FGQPD         (starts at amino acid 28)
              (residues 28-32 of SEQ ID NO:2)
```

There is also another sequence starting at amino acid 37: RSNCKPIPAN (residues 37-46 of SEQ ID NO:2). This sequence is due to a cleavage after a Lysine residue (tryptic like cleavage).

In addition another experiment revealed a sequence starting at position 24:

```
GLFLFGQPDFSYK  (residues of 24-36 of SEQ ID NO:2)
```

Thus, the N-terminus seems to be very heterogeneous, which could also be due to an endopeptidase or protease activity inherent in SARP-1. Mature SARP-1 may occur in several different variants with different N-termini.

Example 4

Transfection of SARP-1 Induces Apoptosis In Vitro

Methods

Fibroblast cell lines (mouse NIH3T3 cells and human AG1518 cells) and primary fibroblast cultures (normal human dermal fibroblasts passage 1-5) (Promocell) were transfected with plasmid pcDNA3.1 containing the SARP-1 cDNA coding sequence or pcDNA3.1 alone (empty vector-mock transfected as a negative control) using either Geneporter 2 (Gene Therapy Systems, San Diego) or Fugene 6 (Life Technologies) transfection reagents according to the manufacturer's recommendations. Apoptosis was measured 24 h after transfection using the TiterTacs 96 well apoptosis assay kit from R&D systems and cells were enumerated using CyQuant dye (Molecular Probes) according to the manufacturer's instructions.

Results

Figure 7:
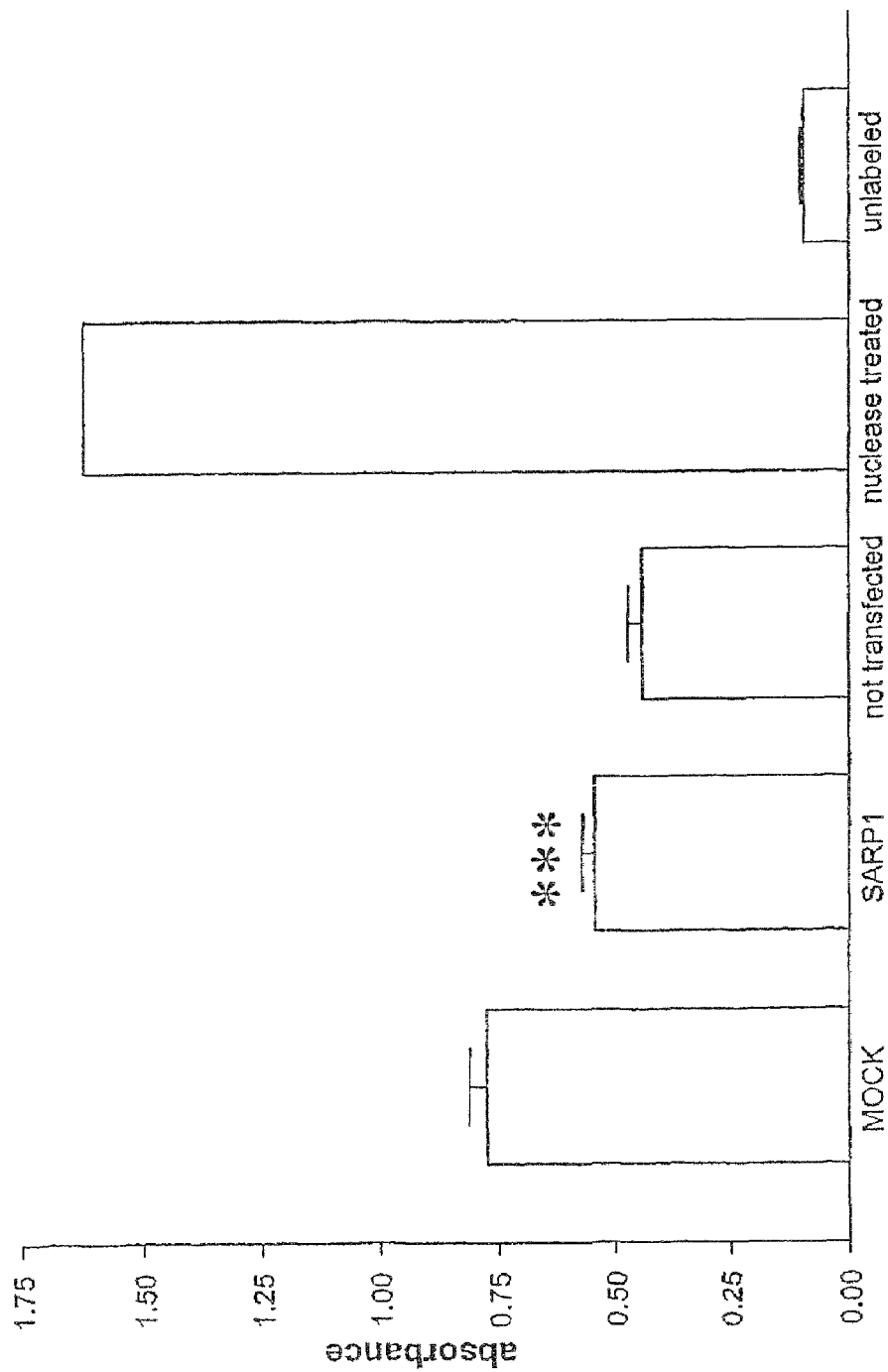
FIG. 7 shows the level of apoptosis in SARP-1 transfected and mock-transfected cells compared to controls. *** is a statistically significant reduction.

In order to assess the effect of SARP-1 on fibroblasts, a fibroblast cell line was transfected with SARP-1 cDNA and the extent of apoptosis was assessed. The results are shown in FIG. 7. Apoptosis in the SARP-1 transfected cells was significantly reduced (P=0.0009) compared to mock (pcDNA3.1) transfected cells indicating that human SARP-1 has activity similar to that reported for its murine homologue. The basal level of apoptosis was determined in non-transfected cells. Nuclease treated NIH 3T3 cells served as the positive control. The column "unlabeled" shows the background staining level, and treatment with nuclease ("nuclease treated") served as a positive control.

Example 5

Effect of SARP-1 on TGFβ1 Production

TGF β1 is a profibrotic cytokine which is upregulated in scleroderma and has been previously associated with the pathogenesis of scleroderma (Kawakami et al., 1998). In order to assess whether SARP-1 downregulates or inhibits TGFβ1 production or secretion by fibroblasts, SARP-1 can be added to fibroblast cultures in form of purified protein. Alternatively, an expression vector comprising SARP-1 cDNA can be transfected into the cells to get a sufficient amount of SARP-1 in the cell culture. Another possibility is to add medium from SARP-1 expressing cells, which may be concentrated in order to achieve sufficient amounts of SARP-1, to fibroblast cultures. Fibroblast cell lines or primary fibroblasts derived from healthy or diseased individuals or from normal or diseased parts of the skin of a scleroderma patient may be used for this experiment.

The amount of TGFβ1 can be measured by ELISA in conditioned medium from cultured cells using the Quantikine ELISA system for TGFβ1 from R&D systems (cat. no. DB100).

Example 6

Effect of SARP-1 Administration on MMP-1 Activity in Human Fibroblasts In Vitro

Methods

The cDNA for human SARP-1 containing the coding sequence for a 6×His tag at the 3' end was subcloned into the baculovirus transfer vector pDEST Fastbac. C-terminal 6×His tagged SARP-1 was produced in Sf5 insect cells infected with recombinant baculovirus and purified by Ni-NTA affinity chromatography.

Low passage number (2-5) human fibroblasts derived from lesional or non-lesional skin from scleroderma patients or from normal subjects were treated in with 0, 100 or 1000 ng/ml recombinant SARP-1 for 24 h. The conditioned medium was harvested and cell debris was removed by centrifugation at 1200 rpm for 10 min at 4 C. MMP-1 activity was measured in the undiluted culture medium using an MMP-1 fluorokine kit (purchased from R&D systems) according to the manufacturer's protocol. MMP-9 activity was also measured in the same samples.

Results

MMP-1 is responsible for the degradation of type I collagen, indicating that the decrease in MMP-1 activity is a contributory factor to one of the underlying defect in scleroderma, which involves excessive collagen deposition.

Figure 8:
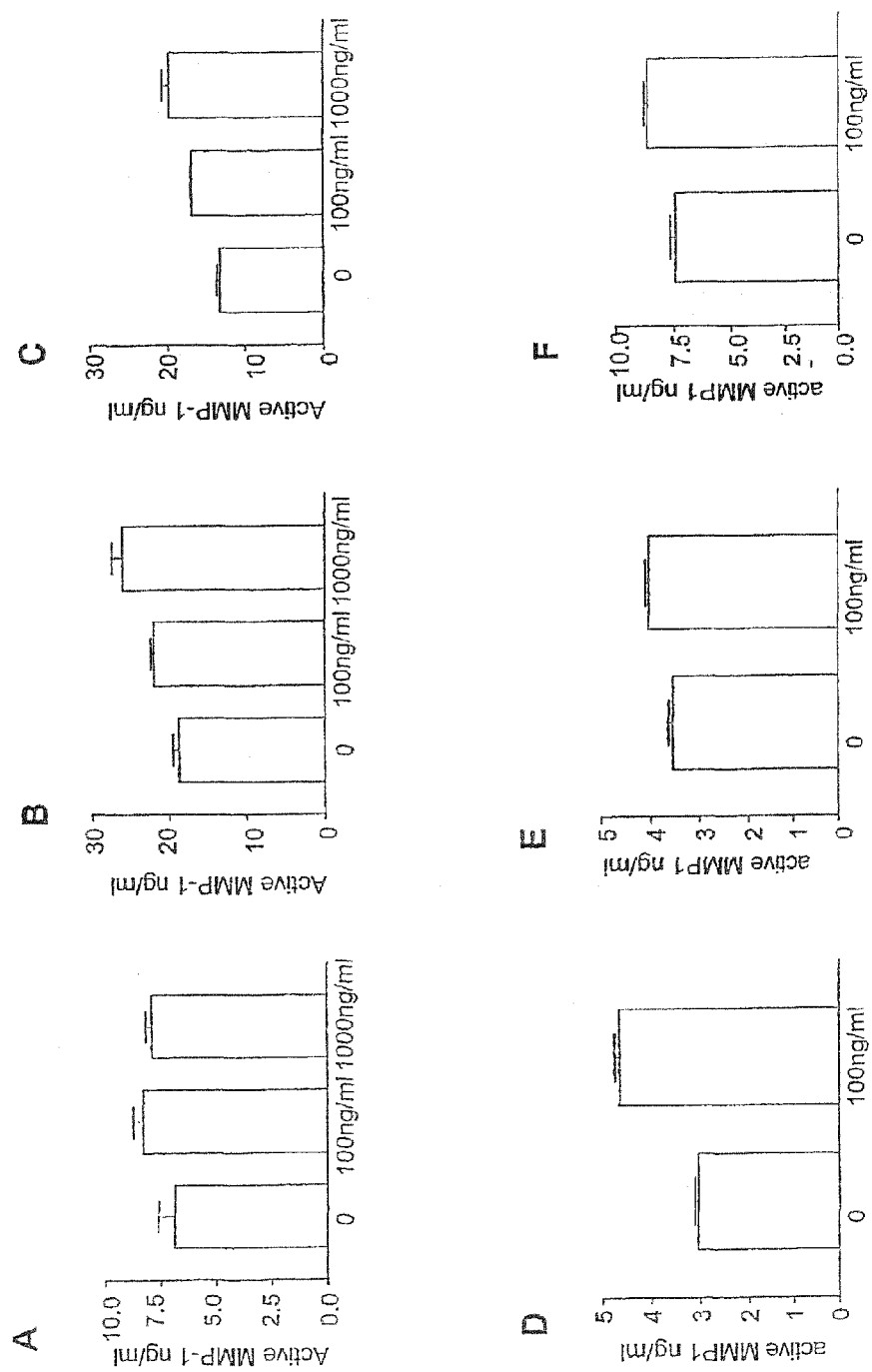
FIG. 8 shows the effect of SARP-1 treatment on total MMP-1 activity in conditioned medium harvested from human dermal fibroblast cultures. The fibroblasts were derived from diseased tissue (A, D, F) or healthy individuals (B, C), or from non-diseased areas of a scleroderma patient (E).

Dermal fibroblasts from scleroderma patients have decreased expression of MMP-1 both at the mRNA level and protein level, in comparison to normal and non-lesional dermal fibroblasts isolated from the same patient. Although the total active MMP-1 detectable varied significantly from patient to patient, SARP-1 treated fibroblasts showed higher MMP-1 activity than untreated fibroblasts, both in abnormal fibroblasts from scleroderma patients (FIG. 8 A, D, F) as well as in fibroblasts derived from non-affected, healthy skin from a sclerodema patient (FIG. 8 E) and in fibroblasts from clinically normal control individuals (FIG. 8 B and C). Results shown are the means of triplicate determinations. In contrast to MMP-1, no effect of SARP-1 was seen on MMP-9 activity (data not shown).

Example 7

Transfection of SARP-1 cDNA Decreases the Activity of the Collagen type1 α2 Promoter in NIH3T3 Fibroblasts Materials and Methods NIH3T3 cells maintained in DMEM containing 2 mM glutamine, 100 units/ml penicillin-streptomycin and 10% FCS were plated at 50% confluency in white walled, transparent bottom tissue culture grade, 96 well plates (Wallac). The next day, cells were co-transfected with pcDNA3.1 SARP-1 and pGL3 vector (Promega) containing the 3.5 kb collagen promoter and luciferase reporter gene (kindly provide by Dr. David Abraham, Royal Free Hospital), using Geneporter transfection reagent according to the manufacturer's instructions. TGFβ (R&D systems, 5 ng/ml) was added 30 h after transfection. Luciferase activity was measured directly in each well, 24-36 h later using the Bright-Glo assay system purchased from Promega.

Results

In order to evaluate if there is any relationship between over expression of SARP-1 and collagen synthesis, the effect of transfection of SARP-1 cDNA on collagen promoter activity in NIH3T3 fibroblasts co-transfected with a Col1α2 promoter-luciferase reporter construct was examined.

Figure 9:
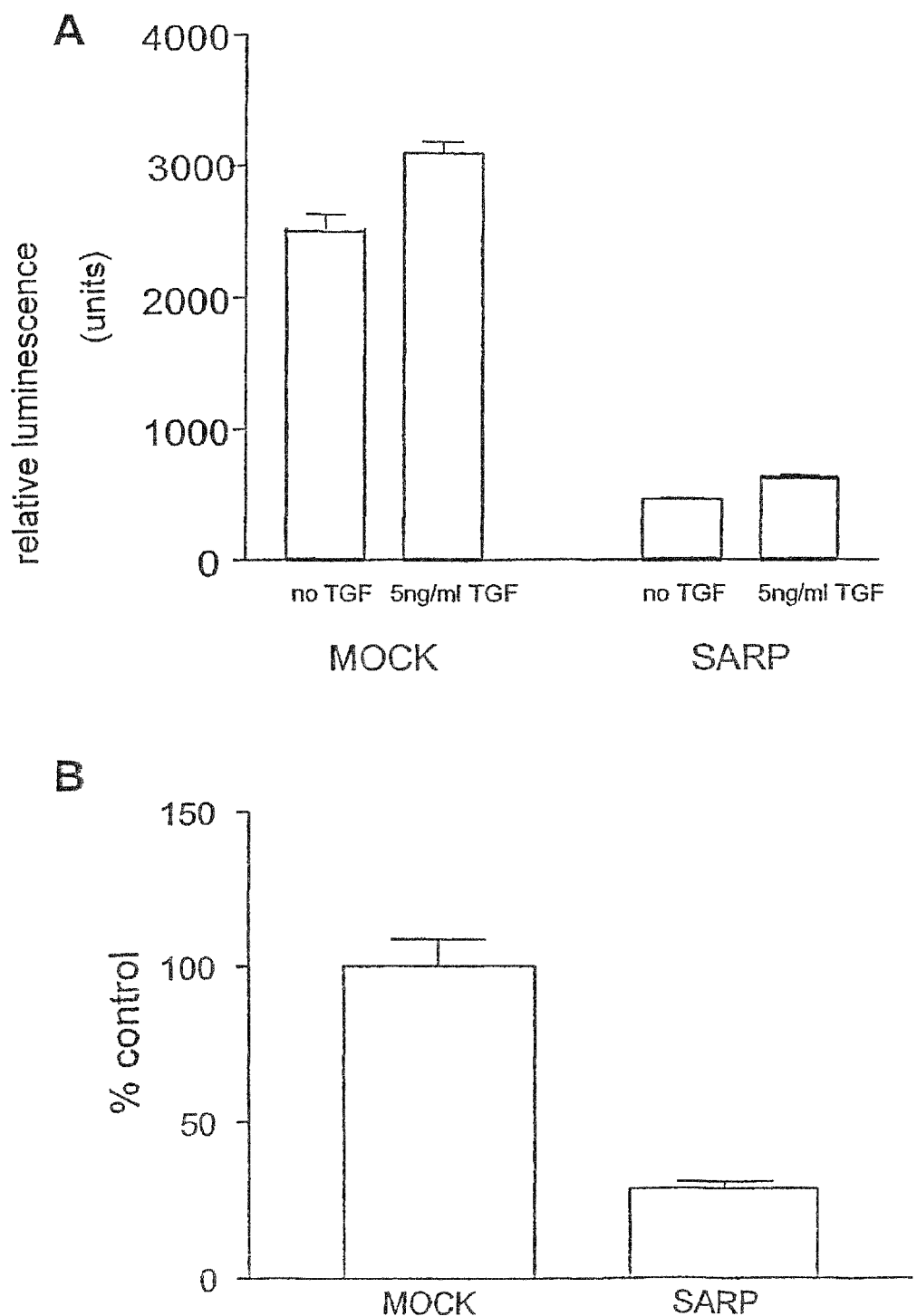
FIG. 9 shows the effect of SARP-1 cotransfection on collagen promoter activity in unstimulated and TGFβ stimulated NIH3T3 cells. (A) indicates the luminescence units measured in the reporter assay, (B) gives the percentage of luminescence with regard to the control.

Cotransfection of SARP-1 cDNA with a collagen promoter—luciferase reporter plasmid indicated that SARP-1 was capable of suppressing not only the basal collagen promoter activity but also the TGFβ induced increase in collagen promoter activity (FIG. 9). These results suggest that the SARP-1 gene product may be involved in the regulation of the collagen promoter activity in vitro either directly or indirectly through SARP-1 mediated signaling events.

Another way of testing the effect of SARP-1 on collagen deposition and/or synthesis and/or secretion in fibroblasts is adding purified SARP-1 to fibroblast cultures. Alternatively, an expression vector comprising SARP-1 cDNA can be transfected into the fibroblasts in order to achieve a sufficient concentration of SARP-1 in the cell culture.

Another possibility is to add medium from SARP-1 expressing cells, which may be concentrated in order to achieve sufficient concentrations of SARP-1, to fibroblast cultures. Fibroblast cell lines or primary fibroblasts derived from healthy or diseased individuals or from normal or diseased parts of the skin of a scleroderma patient may be used for this experiment.

Collagen synthesis can be measured in vitro in cultured human fibroblasts using a capture ELISA system (antibodies purchased from Southern Biotechnology Associates Inc) as described by Shi-wen et al., 1997.

Example 8

Human Dermal Fibroblasts Overexpressing SARP-1 or Treated with Recombinant Human SARP-1 Show Altered mRNA expression of Genes Associated with the Pathology of Scleroderma Materials and Methods Normal human dermal (foreskin) fibroblasts were maintained in fibroblast culture medium (Promocell). Fibroblasts were treated with recombinant human SARP-1 (100 ng/ml) for 4 or 24 h in the presence and absence of human TGFβ1. Cells were harvested after the treatment period and total RNA was isolated using the Trizol™ reagent (Life Technologies) according to the manufacturer's instructions. A 32P-dATP labelled cDNA probe was prepared from the RNA as described above and hybridized to an R&D sytems human cytokine gene filter array and processed as described above.

Results

Although SARP-1 was initially described as an apoptosis related protein, its precise function is unknown. In order to gain an insight into the role of SARP-1 in scleroderma, the effect of treatment of TGFβ pretreated human dermal fibroblasts, which mimics scleroderma phenotyope, with SARP-1 on fibroblast gene expression was measured.

Table IV shows mRNAs affected by treatment of fibroblasts with recombinant SARP-1 after prior stimulation for 4 h with TGFα, which was used to mimic the scleroderma phenotype. Cells were treated with SARP-1 for 24 h. Under these conditions, TGFα and FGF 5 were down regulated. Decreased expression of endoglin, a TGFβ1 binding protein, and increased expression of furin, a protease associated with the activation of matrix metalloproteases, were observed. Another mRNA which was down regulated was TARC. This chemokine is associated with the recruitment of skin homing T cells to inflammatory sites. It is therefore possible that SARP-1 administration may have anti-inflammatory effects. Upregulation of TNFR1 subunit mRNA was also observed. The significance of this observation is unclear as there appears to be much discrepancy in the scientific literature as to whether TNF has a pathogenic or protective role in scleroderma.

In a separate experiment (not shown), regulation of genes in fibroblasts from scleroderma patients had been analyzed in comparison to healthy control fibroblasts. Interestingly, the regulated genes indicated in Table IV had been found to be regulated in scleroderma samples. Those genes found up-regulated in scleroderma fibroblasts were down-regulated after SARP-1 expression in the above model, and those genes found down-regulated were found up-regulated after SARP-1 expression in the above model, further indicating that SARP-1 may have a beneficial effect in treatment of scleroderma.

TABLE IV

| Ratio * | TGFβ treated | TGFβ + SARP-1 treated | Gene |
| --- | --- | --- | --- |
| −1.6 | 1346 | 830 | FGF-5 |
| −2.7 | 788 | 297 | endoglin |
| 3.3 | 157 | 515 | TNFRI |
| 3.3 | 128 | 428 | furin |
| −4.6 | 275 | 60 | TGFα |
| −4.7 | 164 | 34 | TARC |

* Ratio SARP-1/mock represents the ratio TGFα + SARP-1 treated/TGFα alone.

Results shown are based on two independent experiments

Example 9

Assessment of SARP-1 Effects In Vivo in a Murine Model of Disease

The bleomycin-induced lung injury is an accepted model for scleroderma. The disease is induced by intra-tracheal administration of bleomycin (Hattori et al., 2000). Treated mice develop an inflammatory response in the lungs (maximum around day 7) followed by fibrosis that peaks around day 14 post-induction. This model was used to assess the effect of SARP-1 administration in vivo on the development of lung fibrosis. A cell-delivery system (NIH3T3 cells transfected with full length SARP-1 cDNA), was used to generate SARP-1 in vivo.

Methods

Animal Treatments.

Lung fibrosis was induced in mice (20-25 g) by intratracheal administration of bleomycin (0.075 IU) in saline on day 1. Mice were divided into 4 separate groups of 10 animals. One group received an i.p. injection of $10^6$ NIH3T3 cells transfected with SARP-1/pcDNA3.1. A second group received 106 mock transfected (pcDNA3.1 vector) NIH3T3 cells. The third group received 250 μg of anti-TGFβ antibody (Anti Pan TGFβ: Sigma cat. no. T9429) and mice in the final group received saline. All mice were sacrificed at day 14 and lungs were formalin fixed and paraffin embedded for histology. Lung sections were stained with tri-chrome or picro sirius red for collagen (Bancroft J. D. and Stevens A. Theory and Practice of Histological Techniques) and the extent of fibrosis/lung was scored.

Transfection of NIH3T3 Cells

NIH 3T3 cells were transfected with SARP-1/pcDNA3.1 or pcDNA3.1 using the Geneporter 2 reagent as described previously. Twenty four hours after transfection the culture medium was removed and cells were treated with phosphate buffered saline (PBS) containing 1 mM EDTA for 5 min at 37 C. Cells were gently detached with a cell scraper (Costar), centrifuged for 5 min at 4 C to pellet the cells, and resuspended in injection grade saline at a concentration of $10^7$ cells/ml.

Results

SARP-1 Protects Against Bleomycin Induced Lung Fibrosis.

Animals treated with bleomycin alone, or with mock transfected NIH3T3 cells developed significant lung fibrosis (not shown). TGFβ1 is thought to be one of the key agents responsible for the pathological changes leading to fibrosis. An anti TGFβ1 polyclonal antibody has previously been shown to protect against the development of lung fibrosis when administered prophylactically (Yamamoto et al., 1999) and also reduces skin fibrosis in the GvHD model of scleroderma (McCormick et al., 1999). Therefore, this antibody was used as a positive control in these experiments. Anti-TGFβ treated mice did not develop extensive fibrosis of the lungs. However mice treated with SARP-1 transfected cells had a markedly reduced number of fibrotic lesions in the lung when compared to mice treated with bleomycin alone or with mock transfected cells. The effect was comparable or even better than that seen with the anti TGFβ treatment (not shown).

Histological analysis of the lungs shows that the SARP-1 treated animals had close to normal morphology of the lungs with little inflammatory infiltrate and mostly normal alveolar architecture. This morphology resembles the morphology of the anti-TGFβ-treated animals and is in sharp contrast to the abnormal morphology seen in the lungs from mock and untreated animals. In the latter 2 groups, the alveolar spaces are filled by cellular infiltrates and collagen deposition (not shown).

Figure 10:
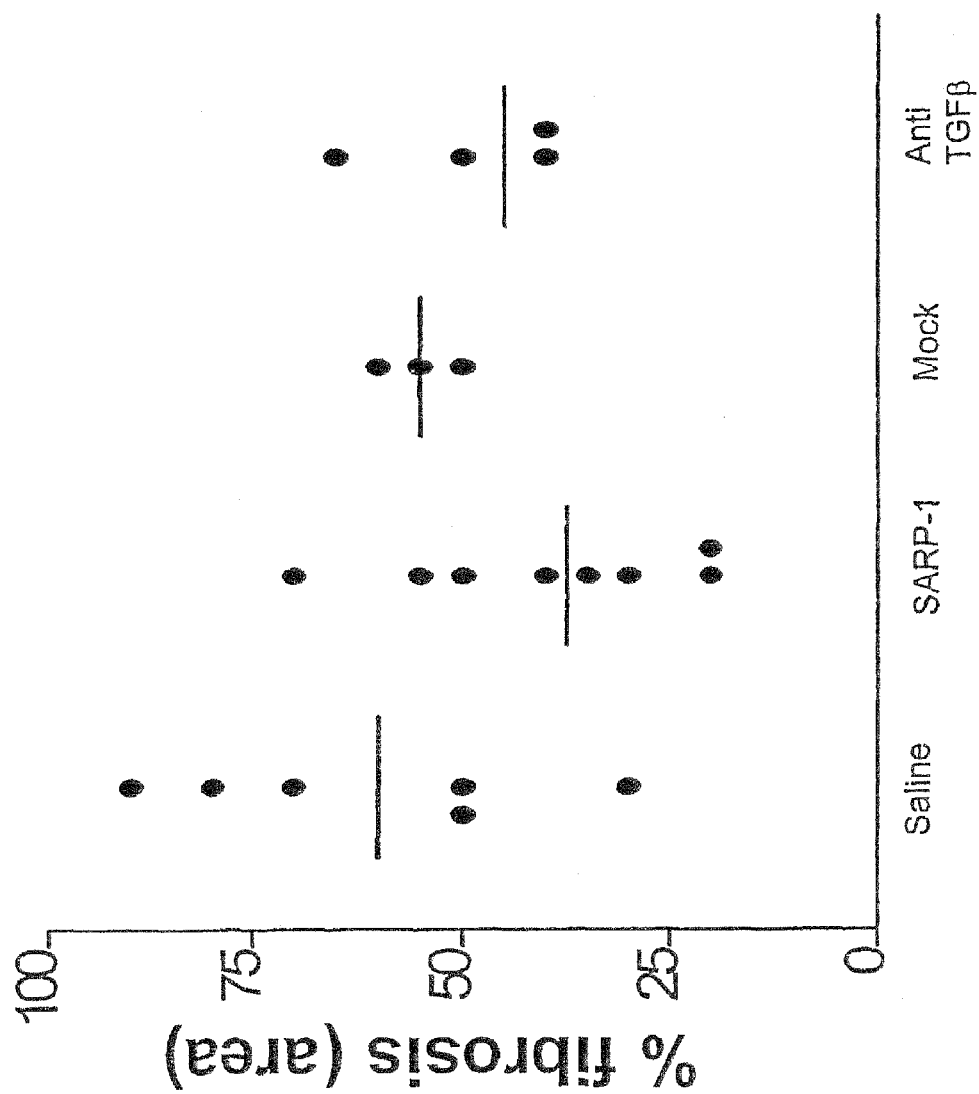
FIG. 10 shows the fibosis score per lung in bleomycin-induced lung fibrosis model. The scores measured in mice having received vehicle, SARP-1-transfected cells, mock transfected cells or anti-TGF therapy is shown. *** is a statistically significant reduction.

The amounts of fibrotic lesions in lungs of the different experimental groups are depicted in FIG. 10. SARP-1 treated mice contained significantly fewer fibrotic lesions as compared to saline or anti-TGFβ treated mice.

Administration of bleomycin can lead to increased mortality. In addition to the protective effects of SARP-1 administration against fibrosis it was also noted that larger numbers of mice survived the treatment (8/10 mice) compared to the saline treated mice (6/10), anti TGFβ treated mice (4/10) and the mock treated mice (3/10). Therefore, SARP-1 treatment even protects from death in the lung fibrosis model, indicating that SARP-1 treatment is clearly superior to anti TGFβ treatment in this experimental setting.

In summary, in this established in vivo model of scleroderma, a beneficial effect of SARP-1 has been demonstrated.

Further in vivo models can be used to test the effect of SARP-1 administration, such as a murine sclerodermatous graft-vs-host disease (Scl GVHD) model for scleroderma. This model reproduces important features of scleroderma including skin thickening, lung fibrosis, and up-regulation of cutaneous collagen mRNA, which is preceded by monocyte infiltration and the up-regulation of cutaneous TGF-beta1 mRNA. The model is described in detail by (McCormick L L et al., 1999).

Example 10

Systemic Delivery of SARP-1 by Intramuscular Injection of Expression Plasmid DNA To demonstrate the role of SARP-1 as a protective factor in scleroderma, mice are transfected in vivo with a plasmid encoding the murine SARP-1 cDNA and are compared to mice transfected with an empty plasmid as control.

Plasmids are injected in both tibial cranial muscles of the anesthetised mouse as previously described (Dimmeler et al., 1997; Mir et al., 1999). Briefly, transcutaneous electric pulses (8 square wave electric pulses of 200 V/cm, 20 msec duration at 2 Hz) are delivered by a PS-15 electropulsator using two stainless steel plate electrodes placed 4.2 to 5.3 mm apart, at each side of the leg.

Then, bleomycin-induced lung fibrosis is as explained in the previous example and development of disease is observed in both SARP-1 transfected and mock transfected animals.

REFERENCES

1. Abraham D., Lupoli S., McWhirter A., Plater-Zyberk C., Piela T. H., Korn J. H., Olsen I. and Black C. (1991) Expression and function of surface antigens on scleroderma fibroblasts. Arthritis Rheum. 34, 1164-1172.
2. Abraham D J, Shiwen X, Black C M, Sa S, Xu Y, Leask A. J Biol. Chem. 2000 May 19; 275(20): 15220-5.
3. Adler P. N., Charlton J and Vinson C. (1987) Dev. Genet. 8, 99-119.
4. Altschul S F et al, J Mol Biol, 215, 403-410, 1990, Altschul S F et al, Nucleic Acids Res., 25:389-3402, 1997
5. Bafico B. A., Gazit A., Pramila T., Finch P. W., Yaniv A. and Aaronson S. A. (1999) Interaction of frizzled related protein (FRP) with Wnt ligands and the frizzled receptor suggests alternative mechanisms for FRP inhibition of Wnt signalling. J. Biol. Chem. 274, 16180-16187.
6. Bancroft J. D. and Stevens A. Theory and Practice of Histological Techniques. Churchill Livingstone, England.
7. Banyai L. and Patthy L. (1999) The NTR module: domains of netrins, secreted frizzled related proteins and type I procollagen C-proteinase enhancer protein are homologous with tissue inhibitors of metalloproteases. Protein Sci. 8, 1636-1642.
8. Black C. M and Denton C. P. (1998) Systemic sclerosis and related disorders. In "Oxford textbook of Rheumatology" (P. G. Maddison, D. A. Isenberg, P. Woo and D. N. Glass, Eds.) pp 771-789, Oxford Univ. Press, New York.

9. Cavalli V, Vilbois F, Corti M, Marcote M J, Tamura K, Karin M, Arkinstall S, Gruenberg J. Mol. Cell 2001 February; 7(2):421-32
10. Chang, J. T.; Esumi, N.; Moore, K.; Li, Y.; Zhang, S.; Chew, C.; Goodman, B.; Rattner, A.; Moody, S.; Stetten, G.; Campochiaro, P. A.; Zack, D. J.: Cloning and characterization of a secreted frizzled-related protein that is expressed by the retinal pigment epithelium. Hum. Molec. Genet. 8: 575-583, 1999
11. Clements P. J. and Furst D. E. (1996) "Systemic Sclerosis" Williama and Williams, Baltimore.
12. Devereux J et al, Nucleic Acids Res, 12, 387-395, 1984.
7. Dimmeler S, Haendeler J, Galle J, Zeiher A M. Oxidized low-density lipoprotein induces apoptosis of human endothelial cells by activation of CPP32-like proteases. A mechanistic clue to the 'response to injury' hypothesis. Circulation 1997;95: 1760-3.
13. Finch P. W., He X., Kelley M. J., Uren A., Schaudies R. P., Popescu N. C., Rudikoff S., Aaronson S. A., Varmus H. E. and Rubin J. S. (1997) Purification and molecular cloning of a screted frizzled related antagonist of Wnt action. Proc. Natl. Acad. Sci. USA 94, 6770-6775.
14. Golub T R, Sionim D K, Tamayo P, Huard C, Gaasenbeek M, Mesirov J P, Coller H, Loh M L, Downing J R, Caligiuri., M A, Bloomfield C D, Lander E S (1999) Molecular classification of cancer: class discovery and class prediction by gene expression monitoring. Science 286, 531-7.
15. Grantham (1974), Science, 185.862-864.
16. Hattori N., Degen J. L., Sisson T. H., Liu H., Moore B. B., Pandrangi R. G., Simon R. H. and Drew A. F. (2000) Bleomycin induced pulmonary fibrosis in fibrinogen null mice. J. Clin. Invest. 106, 1341-135
17. Kawakami T., Ihn H., Xu W., Smith E., LeRoy C. and Trojanowska M (1998) Increased expression of TGF beta receptors by scieroderma fibroblasts: evidence for contribution of autocrine TGF-beta signalling to scleroderma phenotype. J. Invest. Dermatol. 10, 47-51.
18. Krein, P M, Huang Y amd Winston B W (2001). Expert Opin. Ther. Patents 11(7): 1065-1079.
19. Leighton, C. Drugs 2001 61(3), 419-427.
20. Leimeister C, Bach A, Gessler M. Mech Dev 1998 Jul;75 (1-2):29-42.
21. LeRoy E. C. (1974) Increased collagen synthesis by scleroderma skin fibroblasts in vitro. J. Clin. Invest. 54, 880-889.
22. Lin K, Wang S, Julius M A, Kitajewski J, Moos M Jr, Luyten F P, Proc Natl Acad Sci USA 1997 Oct. 14; 94(21): 11196-200.
23. Martini, Maccario, Ravelli et al., Arthritis Rheum. 1999, 42, 807-811.
24. McCormick L L, Zhang Y, Tootell E, Gilliam A C J. Immunol. 163(10) 5693 (1999).
25. Melkonyan H. S., Chang W. C., Shapiro J. P., Mahadevappa M., Fitzpatrick P. A., Kiefer M. C., Tomei L. D. and Umansky S. R. (1997) SARPs: a family of secreted apoptosis-related proteins. Proc. Natl. Acad. Sci. USA 94, 13696-13641.
26. Miller J. R., Hocking A. M., Brown J. D. and Moon R. T. (1999) Mechanism and function of signal transduction by the Wnt/1 catenin and Wnt/Ca2+ pathways. Oncogene 18, 7860-7872.
8. Mir L M, Bureau M F, Gehi J, Rangara R, Rouy D, Caillaud J M, Dellere P, Branellec D, Schwartz B, Scherman D. High efficiency gene transfer into skeletal muscle mediated by electric pulses. Proc Natl Acad Sci USA 1999; 96:4262-7.
9. Pearson W R, Methods in Enzymology, 183, 63-99, 1990
10. Pearson W R and Lipman D J, Proc Nat Acad Sci USA, 85, 2444-2448, 1988
27. Rattner A., Hsieh J-C., Smallwood P. M., Gilbert D. J., Copeland N. G., Jenkins N. A., Nathans J. (1997) A family of secreted proteins contain homology to the cysteine rich ligand binding domain of frizzled receptors. Proc. Natl. Acad. Sci. USA 94, 2859-2863.
28. Shevchenko A., Wilm M., Vorm O. and Mann M. (1996) Mass spectrometric sequencing of proteins silver-stained polyacrylamide gels. Anal. Chem., 68:850-858
29. Silman A. J. (1991) Moratlity from scieroderma in England and Wales 1968-1975. Ann. Rheu. Dis. 50, 95-96.
30. Shi-wen X., Denton C. P., McWhirter A., Bou-Gharios G., Abraham D. J., du Bois R. M. and Black C. M. (1997) Scleroderma lung fibroblasts exhibit elevated and dysregulated collagen type I biosynthesis. Arthritis Rheum. 40, 1237-1244.
31. Shi-wen X., Denton C. P., Dashwood M. R., Holmes A., Bou-Gharios G., Pearson J. D., Black C. M. and Abraham D. J. (2000) Fibroblast matrix gene expression and connective tissue remodelling: role of endothelin-1. J. Invest. Dermatol. (in press).
32. Smalley M. J. and Dale T. C. (1999) Wnt signalling in mammalian development and cancer. Cancer and Metastasis Rev. 18, 215-230.
33. Smith and Waterman J Mol Biol, 147,195-197, 1981, Advances in Applied Mathematics, 2, 482-489, 1981.
34. Strehlow D. and Korn J (1998) Biology of the scleroderma fibroblast. Curr. Opin. Rheumatol. 10, 572-578.
35. Smith, Textbook of the Autoimmune Diseases, Edited by Lahita, Chiorazzi and Reeves, Lippincott Williams & Wilkins, Philadelphia 2000.
36. Von Heijne G. (1986) Nucleic Acids Res. 14, 4683-4690.
37. Wigley F. M. and Sule S. D. (2001) Expert Opinions on Investigational Drugs 10(1) 31-48.
38. Wigley F. M. and Boling C. L. (2000) The treatment of scleroderma. 2, 276-292.
39. Wilm M., Shevchenko A., Houthaeve T., Breit S., Schweigerer L., Fotsis T. and Mann M. (1996) Femtomole sequencing of proteins from polyacrylamide gels by nanoelectrospray mass spectrometry. Nature, 379:466-469
40. Yamamoto T. S., Takagawa L., Katayama I. and Nishioka K. (1999) Anti-sclerotic effect of transforming growth factor-α antibody in a mouse model of bleomycin induced scleroderma. Clin Immunol. 92, 6.

What is claimed is:

1. A method for treating liver cirrhosis or interstitial pulmonary fibrosis, comprising administering to a patient in need thereof a polypeptide that binds to Wnt protein to competitively inhibit the binding of Wnt protein to its receptor and to treat liver cirrhosis or interstitial pulmonary fibrosis, wherein said polypeptide is selected from the group consisting of:
- a) mature secreted apoptosis-related protein 1 (SARP-1) comprising at least 90% sequence identity to amino acids 21 to 295 of SEQ ID NO:2;
- b) a fragment of a) comprising at least the cysteine rich frizzled domain thereof;
- c) a polypeptide comprising SEQ ID NO:2;
- d) a polypeptide comprising amino acids 21 to 295 of SEQ ID NO:2;
- e) a polypeptide comprising amino acids 24 to 295 of SEQ ID NO:2;
- f) a polypeptide comprising amino acids 25 to 295 of SEQ ID NO:2;
- g) a polypeptide comprising amino acids 26 to 295 of SEQ ID NO:2;
- h) a polypeptide comprising amino acids 27 to 295 of SEQ ID NO:2;
- i) a polypeptide comprising amino acids 28 to 295 of SEQ ID NO:2;
- j) a polypeptide comprising amino acids 37 to 295 of SEQ ID NO:2;
- k) a mutein of any of (a) to (j), wherein the amino acid sequence of said mutein has at least 90% sequence identity to at least one of the sequences in (a) to (j);
- l) the mutein of (k), wherein any changes in the amino acid sequence are conservative amino acid substitutions to the amino acid sequences in (k);
- m) a salt, an isoform of (a)-(l), or a fusion protein of any of (a) to (l).

2. The method of claim 1, wherein the polypeptide is glycosylated.

3. The method of claim 1, wherein said (m) fused protein is a fusion between said polypeptide and an immunoglobulin.

4. The method of claim 1, wherein said polypeptide is present in a pharmaceutical composition that further comprises an interferon.

5. The method of claim 4, wherein the interferon is interferon-β.

6. The method of claim 1, wherein said polypeptide is administered systemically.

7. The method of claim 1, wherein said polypeptide is administered by intramuscular injection.

8. The method of claim 1, wherein said polypeptide is administered by inhalation.

9. The method of claim 1, wherein said polypeptide is administered subcutaneously.

* * * * *

SEQUENCE LISTING

<160> NUMBER OF SEQ ID NOS: 6

<210> SEQ ID NO 1
<211> LENGTH: 912
<212> TYPE: DNA
<213> ORGANISM: Homo sapiens -continued

<400> SEQUENCE: 1

```
gccaagcttc ccacgatgct gcagggccct ggctcgctgc tgctgctctt cctcgcctcg      60
cactgctgcc tgggctcggc gcgcgggctc ttcctctttg gccagcccga cttctcctac     120
aagcgcagca attgcaagcc catcccggcc aacctgcagc tgtgccacgg catcgaatac     180
cagaacatgc ggctgcccaa cctgctgggc acgagaccat gaaggaggt gctggagcag     240
gccggcgctt ggatcccgct ggtcatgaag cagtgccacc cggacaccaa gaagttcctg     300
tgctcgctct tcgcccccgt ctgcctcgat gacctagacg agaccatcca gccatgccac     360
tcgctctgcg tgcaggtgaa ggaccgctgc gccccggtca tgtccgcctt cggcttcccc     420
tggcccgaca tgcttgagtg cgaccgtttc ccccaggaca cgacctttg catccccctc      480
gctagcagcg accacctcct gccagccacc gaggaagctc caaaggtatg tgaagcctgc     540
aaaaataaaa atgatgatga caacgacata atggaaacgc tttgtaaaaa tgattttgca     600
ctgaaaataa aagtgaagga gataacctac atcaaccgag ataccaaaat catcctggag     660
accaagagca agaccattta caagctgaac ggtgtgtccg aaagggacct gaagaaatcg     720
gtgctgtggc tcaaagacag cttgcagtgc acctgtgagg agatgaacga catcaacgcg     780
ccctatctgg tcatgggaca gaaacagggt ggggagctgg tgatcacctc ggtgaagcgg     840
tggcagaagg ggcagagaga gttcaagcgc atctcccgca gcatccgcaa gctgcagtgc     900
tagctcgagc gc                                                         912
```

<210> SEQ ID NO 2
<211> LENGTH: 295
<212> TYPE: PRT
<213> ORGANISM: Homo sapiens

<400> SEQUENCE: 2

```
Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190
```

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Lys Gln Gly Gly Glu Leu Val Ile Thr Ser
                260                 265                 270

Val Lys Arg Trp Gln Lys Gly Gln Arg Glu Phe Lys Arg Ile Ser Arg
                275                 280                 285

Ser Ile Arg Lys Leu Gln Cys
                290                 295

<210> SEQ ID NO 3
<211> LENGTH: 30
<212> TYPE: DNA
<213> ORGANISM: homo sapiens

<400> SEQUENCE: 3
gccaagcttc ccacgatgct gcagggccct                                    30

<210> SEQ ID NO 4
<211> LENGTH: 30
<212> TYPE: DNA
<213> ORGANISM: homo sapiens

<400> SEQUENCE: 4
gcgctcgagc tagcactgca gcttgcggat                                    30

<210> SEQ ID NO 5
<211> LENGTH: 295
<212> TYPE: PRT
<213> ORGANISM: Mus musculus

<400> SEQUENCE: 5

Met Pro Arg Gly Pro Ala Ser Leu Leu Leu Val Leu Ala Ser His
1               5                   10                  15

Cys Cys Leu Gly Ser Ala Arg Gly Leu Phe Leu Phe Gly Gln Pro Asp
                20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
                100                 105                 110

Pro Cys His Ser Leu Cys Val Gln Val Lys Asp Arg Cys Ala Pro Val
            115                 120                 125

Met Ser Ala Phe Gly Phe Pro Trp Pro Asp Met Leu Glu Cys Asp Arg
        130                 135                 140

Phe Pro Gln Asp Asn Asp Leu Cys Ile Pro Leu Ala Ser Ser Asp His
145                 150                 155                 160

```
-continued

Leu Leu Pro Ala Thr Glu Glu Ala Pro Lys Val Cys Glu Ala Cys Lys
            165                 170                 175

Thr Lys Asn Glu Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
            195                 200                 205

Asp Thr Lys Ile Ile Leu Glu Thr Lys Ser Lys Thr Ile Tyr Lys Leu
        210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
            245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
            275                 280                 285

Ser Ile Arg Lys Leu Gln Cys
    290                 295

<210> SEQ ID NO 6
<211> LENGTH: 13
<212> TYPE: PRT
<213> ORGANISM: Artificial
<220> FEATURE:
<223> OTHER INFORMATION: synthetic

<400> SEQUENCE: 6

Glu Phe Gly Ala Gly Leu Val Leu Gly Gly Gln Phe Met
1               5                   10
```